(12) United States Patent
Annapragada et al.

(10) Patent No.: US 10,124,078 B2
(45) Date of Patent: Nov. 13, 2018

(54) LIPID-BASED NANOPARTICLES

(71) Applicants: BOARD OF REGENTS OF THE UNIVERSITY OF HOUSTON SYSTEM, Houston, TX (US); BOARD OF REGENTS OF THE UNIVERSITY OF TEXAS SYSTEM, Austin, TX (US); ALZECA BIOSCIENCES, LLC, Houston, TX (US)

(72) Inventors: Ananth V. Annapragada, Manvel, TX (US); Jason L. Eriksen, Houston, TX (US); Eric A. Tanifum, Katy, TX (US); Indrani Dasgupta, Frederick, MD (US); Stephen C. Cook, Houston, TX (US)

( * ) Notice: Subject to any disclaimer, the term of this patent is extended or adjusted under 35 U.S.C. 154(b) by 0 days.

(21) Appl. No.: 15/797,816

(22) Filed: Oct. 30, 2017

(65) Prior Publication Data
US 2018/0043039 A1    Feb. 15, 2018

Related U.S. Application Data

(63) Continuation-in-part of application No. 13/441,816, filed on Apr. 6, 2012, now Pat. No. 9,801,957.

(60) Provisional application No. 61/472,605, filed on Apr. 6, 2011.

(51) Int. Cl.
*A61K 9/127* (2006.01)
*A61K 49/18* (2006.01)
*C08G 65/335* (2006.01)

(52) U.S. Cl.
CPC ........ *A61K 49/1812* (2013.01); *A61K 9/1273* (2013.01); *C08G 65/3353* (2013.01)

(58) Field of Classification Search
CPC ............ A61K 2300/00; A61K 49/1812; A61K 38/13; A61K 49/126; A61K 49/0034; A61K 49/0084; A61K 49/10; A61K 45/06; A61K 31/12; A61K 31/353; A61K 3/4152; A61K 31/4196; A61K 31/444; A61K 31/4965; A61K 31/5415; A61K 31/6615; A61K 38/00; A61K 49/0466; A61K 38/05; A61K 38/08; A61K 38/10; A61K 38/45; A61K 47/64; C08G 65/3353
See application file for complete search history.

(56) References Cited

PUBLICATIONS

Klunk et al., Imaging Abeta Plaques in Living Transgenic Mice with Multiphoton Microscopy and Methoxy-X04, a Systemically Administered Congo Red Derivative, Sep. 2002, Journal of Neuropathology and Experimenta Neurology, vol. 61, No. 9, pp. 797-805 (Year: 2002).*

* cited by examiner

*Primary Examiner* — Nanette Holloman
(74) *Attorney, Agent, or Firm* — Benesch Friedlander Coplan & Aronoff LLP; Benjamin E. Kern; Kraig K. Anderson

(57) ABSTRACT

Lipid-based nanoparticle compositions are provided. The compositions generally comprise lipid-hydrophilic polymer-amyloid binding ligand conjugates, and may be liposomal compositions. The compositions, including the liposomal compositions, may be useful for imaging and/or the treatment of amyloid-β plaque deposits characteristic of Alzheimer's Disease.

20 Claims, 13 Drawing Sheets

LIPID-BASED NANOPARTICLES

CROSS-REFERENCE TO RELATED APPLICATIONS

This application is a continuation-in-part of U.S. patent application Ser. No. 13/441,816, filed on Apr. 6, 2012, and claims priority from U.S. Provisional Pat. App. No. 61/472,605, filed on Apr. 6, 2011. Each of these documents is entirely incorporated by reference herein.

STATEMENT REGARDING FEDERALLY SPONSORED RESEARCH OR DEVELOPMENT

This invention was made with Government support under W81XWH-09-2-0139 awarded by the U.S. Department of Defense. The Government has certain rights in this invention.

BACKGROUND

Alzheimer's disease ("AD") is a neurodegenerative illness characterized by memory loss and other cognitive deficits. AD is the most common form of dementia and affects one in every eight people over the age of 65 and one in every two over the age of 85. AD is the sixth leading cause of death in the United States. Over 5.5 million Americans suffer from AD, with an estimated annual cost of $200 billion USD. By 2050, it is projected that AD will affect over 20 million Americans at an annual price tag of $1.1 Trillion USD (in 2011 dollars). Around the world, the estimated figures for the year 2011 were over 37 million sufferers, at an associated cost of over $600 billion (USD).

A significant hindrance to identification and treatment of AD is the paucity of effective diagnostic tests. At present, AD is typically only conclusively diagnosed by post-mortem histopathological analysis. Diagnosis in living patients relies primarily on psychiatric testing to detect cognitive impairment. However, the major neuropathological hallmarks of AD—extracellular amyloid-β ("Aβ") plaque deposits and intracellular neurofibrillary tangles—manifest long before clinical symptoms are discernable. Aβ deposits also represent a major risk factor for hemorrhagic stroke.

Thus, a need exists for compositions and methods suitable for in vivo imaging of intracranial Aβ plaque deposits, for diagnostic purposes and to monitor the effectiveness of therapies targeted at preventing Aβ plaque deposits. Current approaches suffer from one or more of a myriad of drawbacks, including invasiveness, lack of specificity of the imaging agents for Aβ deposits, unsuitable resolution, the inability of the imaging agents to cross the blood-brain barrier ("BBB") effectively, a tendency on the part of the imaging agents to induce an unsuitably high pro-inflammatory response in the vicinity of the Aβ deposits, and unsuitable cytotoxicity. Thus, a further need exists for compositions and methods that are suitable for in vivo imaging of intracranial Aβ plaque deposits, but that do not suffer from one or more of the drawbacks of current approaches. A still further need exists for compositions and methods suitable to treat or aid treatment or prophylaxis of AD.

SUMMARY

In one embodiment, a liposomal composition is provided. The liposomal composition may include a membrane. The membrane may include a first phospholipid. The membrane may include cholesterol. The membrane may include a second phospholipid. The second phospholipid may be derivatized with a polymer. The membrane may include a third phospholipid. The third phospholipid may be a phospholipid-polymer-aromatic compound conjugate. The phospholipid-polymer-aromatic compound conjugate may be represented by:

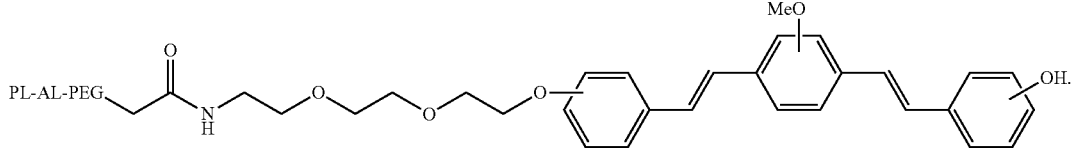

PL may be a phospholipid. AL may be an aliphatic linkage. PEG may be a polyethylene glycol polymer. The membrane may include a nonradioactive magnetic resonance imaging (MRI) contrast enhancing agent at least one of encapsulated by or bound to the membrane.

In one embodiment, a method for imaging amyloid deposits in a patient is provided. The method may include introducing into the patient a detectable quantity of a liposomal composition. The liposomal composition may include a membrane. The membrane may include a first phospholipid. The membrane may include cholesterol. The membrane may include a second phospholipid. The second phospholipid may be derivatized with a polymer. The membrane may include a third phospholipid. The third phospholipid may be a phospholipid-polymer-aromatic compound conjugate. The phospholipid-polymer-aromatic compound conjugate may be represented by:

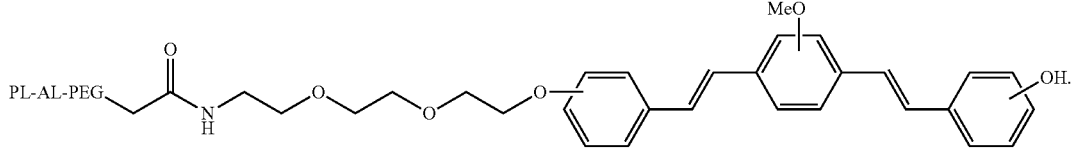

PL may be a phospholipid. AL may be an aliphatic linkage. PEG may be a polyethylene glycol polymer. The membrane may include a nonradioactive magnetic resonance imaging (MRI) contrast enhancing agent at least one of encapsulated by or bound to the membrane. The method may include allowing sufficient time for the liposomal composition to be associated with one or more amyloid deposits. The method may include detecting the liposomal composition associated with the one or more amyloid deposits.

In one embodiment, a phospholipid-polymer-aromatic compound conjugate is provided. The phospholipid-polymer-aromatic compound conjugate may be represented by:

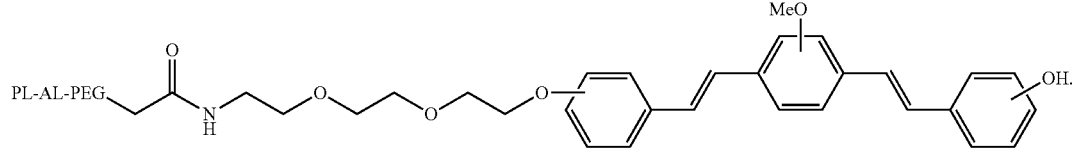

PL may be a phospholipid. AL may be an aliphatic linkage. PEG may be a polyethylene glycol polymer.

BRIEF DESCRIPTION OF THE DRAWINGS

In the accompanying figures, chemical formulas, chemical structures, and experimental data are given that, together with the detailed description provided below, describe example embodiments of the claimed invention.

DETAILED DESCRIPTION

Figure 1:
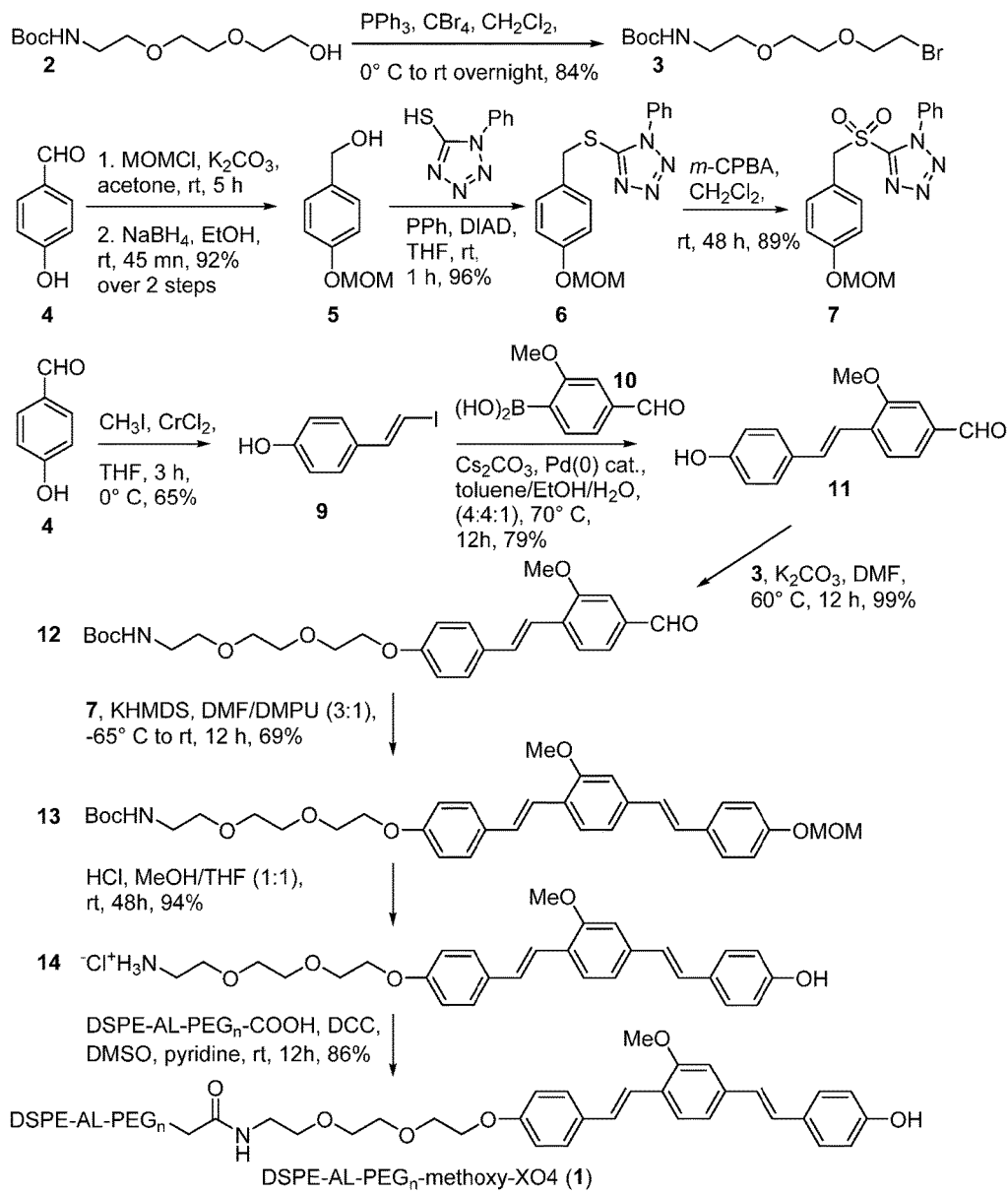
FIG. 1 illustrates an example schematic for the synthesis of the phospholipid-hydrophilic polymer-aromatic ligand conjugate, DSPE-AL-PEG$_n$-methoxy-XO4 ("Me-XO4").

In one embodiment, a liposomal composition is provided. The liposomal composition may include a membrane. The membrane may include a first phospholipid. The membrane may include cholesterol. The membrane may include a second phospholipid. The second phospholipid may be derivatized with a polymer. The membrane may include a third phospholipid. The third phospholipid may be a phospholipid-polymer-aromatic compound conjugate. The phospholipid-polymer-aromatic compound conjugate may be represented by PL-AL-PEG-aromatic compound, wherein PL may be a phospholipid, AL may be an aliphatic linkage, PEG may be a polyethylene glycol polymer, and the aromatic compound may be represented by one of Formulas I, II, III, IV, V, VI, and VII as described herein. The membrane may include a nonradioactive magnetic resonance imaging (MRI) contrast enhancing agent at least one of encapsulated by or bound to the membrane.

In one embodiment, a liposomal composition is provided. The liposomal composition may include a membrane. The membrane may include a first phospholipid. The membrane may include cholesterol. The membrane may include a second phospholipid. The second phospholipid may be derivatized with a polymer. The membrane may include a third phospholipid. The third phospholipid may be a phospholipid-polymer-aromatic compound conjugate. The phospholipid-polymer-aromatic compound conjugate may be represented by:

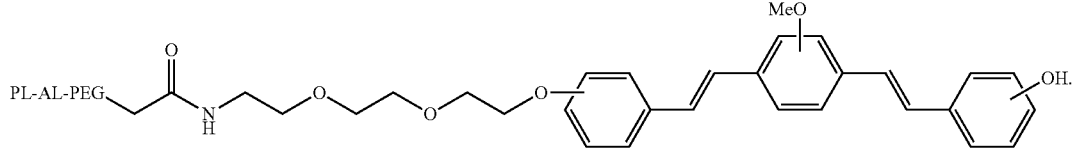

PL may be a phospholipid. AL may be an aliphatic linkage. PEG may be a polyethylene glycol polymer. The membrane may include a nonradioactive magnetic resonance imaging (MRI) contrast enhancing agent at least one of encapsulated by or bound to the membrane.

As used herein, an "aliphatic linkage" represented by AL includes any aliphatic group useful for linking between a phospholipid and a PEG polymer. Such aliphatic linkages may include, for example, $C_2$-$C_{10}$ alkylene groups, which may include heteroatoms via one or more moieties such as amides, carbamates, and the like. For example, in the compound below:

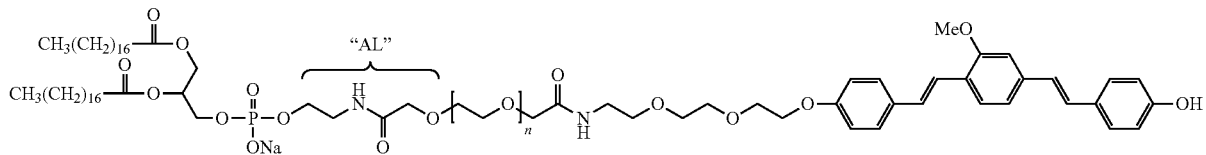

the aliphatic linkage AL, —CH$_2$CH$_2$NH(C=O)CH$_2$O—, includes an amide moiety. Further, for example, in the compound below:

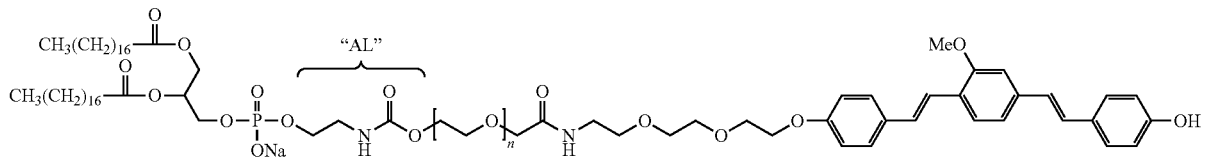

the aliphatic linkage AL, —CH$_2$CH$_2$NH(C=O)O— includes a carbamate moiety. AL may include aliphatic linkages derived from dicarboxylic acids, such as succinic acid, and may include two amides, two carbamates, an amide and a carbamate, and the like.

Such aliphatic linkages are known in the art for linking between a phospholipid and a PEG polymer, and may be found, for example, in commercial sources of phospholipid-PEG compounds, and functionalized phospholipid-PEG conjugation precursors, which may be represented as PL-AL-PEG-NH$_2$, PL-AL-PEG-CO$_2$H, and the like. It should be noted that it is common in the art and in commercial sources to refer to such compounds in abbreviated form without reference to the aliphatic linkage, where the presence of the aliphatic linkage is implied. For example, 1,2-distearoyl-sn-glycero-3-phosphoethanolamine-N-[methoxy(polyethylene glycol)-2000] CAS No. 147867-65-0, in which the aliphatic linking group is the amide containing group —CH$_2$CH$_2$NH(C=O)CH$_2$O—, is commonly referred to in the art and commercially as "DSPE-mPEG-2000." Herein, the aliphatic linkages AL are specifically recited for the compounds found in the claims. Commercial materials recited herein in the conventional abbreviated manner, such as "DSPE-mPEG-2000," should be understood to include corresponding aliphatic linkages.

Further, it has now been now found for such compounds that among various commercial sources and even different lots from the same commercial source may contain a mixture of compounds with different aliphatic linkers, e.g., a mixture of compounds having amine and carbamate aliphatic linkers. The results described in the Examples have been examined and have been found similar using conjugates with AL including carbamate, amide, and mixtures thereof. More information may be found in the Examples.

Accordingly, in various embodiments, AL may include a carbamate or an amide. The liposomes, methods, and conjugates described herein may include phospholipid-polymer-aromatic compound conjugates wherein AL includes a carbamate, an amide, or a mixture of such conjugates.

In some embodiments, the phospholipid-polymer-aromatic compound conjugate may include a compound represented by:

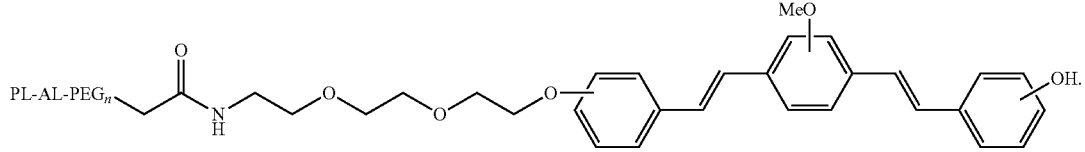

wherein n represents a degree of polymerization of the polyethylene glycol polymer, and may be about 10 to about 100, about 30 to about 80, or about 30 to about 60.

In several embodiments, the phospholipid-polymer-aromatic compound conjugate may include a compound represented by:

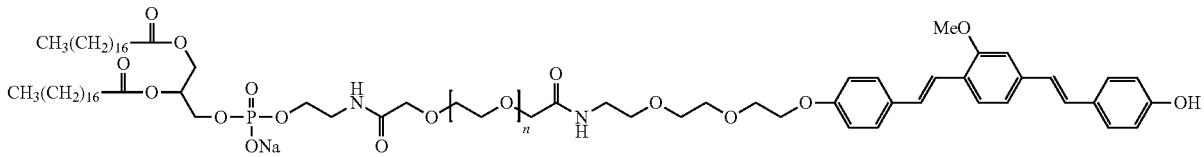

wherein n may be about 10 to about 100, about 30 to about 80, or about 30 to about 60.

In various embodiments, the nonradioactive MRI contrast enhancing agent may include gadolinium.

In some embodiments, the liposomal composition may include DPPC as the first phospholipid. The liposomal composition may include the cholesterol. The liposomal composition may include DSPE-AL-mPEG-2000 as the second phospholipid. The liposomal composition may include the third phospholipid including a compound represented by:

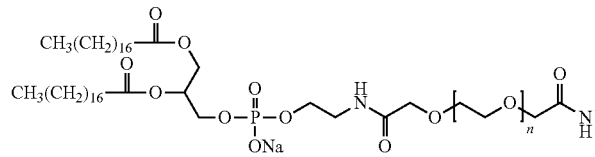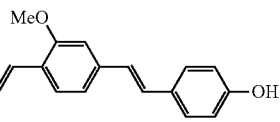

wherein n may be about 10 to about 100, about 30 to about 80, or about 30 to about 60. The nonradioactive magnetic resonance imaging (MRI) contrast enhancing agent may include Gd-DTPA-BSA.

In one embodiment, a method for imaging amyloid deposits in a patient is provided. The method may include introducing into the patient a detectable quantity of a liposomal composition. The liposomal composition may include a membrane. The membrane may include a first phospholipid. The membrane may include cholesterol. The membrane may include a second phospholipid. The second phospholipid may be derivatized with a polymer. The membrane may include a third phospholipid. The third phospholipid may be a phospholipid-polymer-aromatic compound conjugate. The phospholipid-polymer-aromatic compound conjugate may be represented by PL-AL-PEG-aromatic compound, wherein PL may be a phospholipid, AL may be an aliphatic linkage, PEG may be a polyethylene glycol polymer, and the aromatic compound may be represented by one of Formulas I, II, III, IV, V, VI, and VII as described herein. The membrane may include a nonradioactive magnetic resonance imaging (MRI) contrast enhancing agent at least one of encapsulated by or bound to the membrane. The method may include allowing sufficient time for the liposomal composition to be associated with one or more amyloid deposits. The method may include detecting the liposomal composition associated with the one or more amyloid deposits.

In one embodiment, a method for imaging amyloid deposits in a patient is provided. The method may include introducing into the patient a detectable quantity of a liposomal composition. The liposomal composition may include a membrane. The membrane may include a first phospholipid. The membrane may include cholesterol. The membrane may include a second phospholipid. The second phospholipid may be derivatized with a polymer. The membrane may include a third phospholipid. The third phospholipid may be a phospholipid-polymer-aromatic compound conjugate. The phospholipid-polymer-aromatic compound conjugate may be represented by:

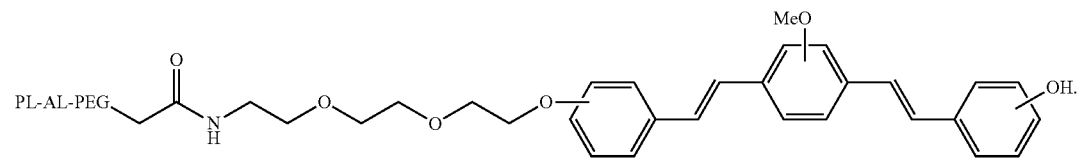

PL may be a phospholipid. AL may be an aliphatic linkage. PEG may be a polyethylene glycol polymer. The membrane may include a nonradioactive magnetic resonance imaging (MRI) contrast enhancing agent at least one of encapsulated by or bound to the membrane. The method may include allowing sufficient time for the liposomal composition to be associated with one or more amyloid deposits. The method may include detecting the liposomal composition associated with the one or more amyloid deposits.

In various embodiments of the method, the nonradioactive MRI contrast enhancing agent may include gadolinium. The method may include detecting using magnetic resonance imaging.

In some embodiments of the method, the phospholipid-polymer-aromatic compound conjugate may include a compound represented by:

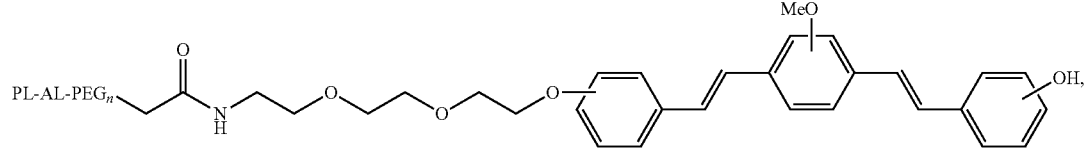

wherein n represents a degree of polymerization of the polyethylene glycol polymer, and may be about 10 to about 100, about 30 to about 80, or about 30 to about 60.

In some embodiments of the method, the phospholipid-polymer-aromatic compound conjugate may include a compound represented by:

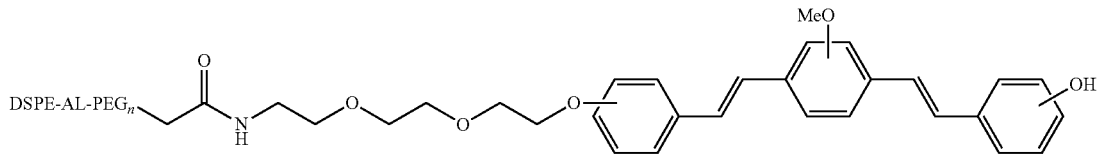

wherein n represents a degree of polymerization of the polyethylene glycol polymer, and may be about 10 to about 100, about 30 to about 80, or about 30 to about 60.

In several embodiments of the method, the phospholipid-polymer-aromatic compound conjugate may include a compound represented by:

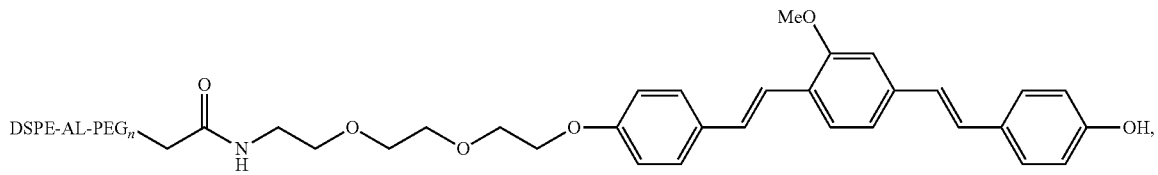

wherein n represents a degree of polymerization of the polyethylene glycol polymer, and may be about 10 to about 100, about 30 to about 80, or about 30 to about 60.

In various embodiments of the method, the phospholipid-polymer-aromatic compound conjugate may include a compound represented by:

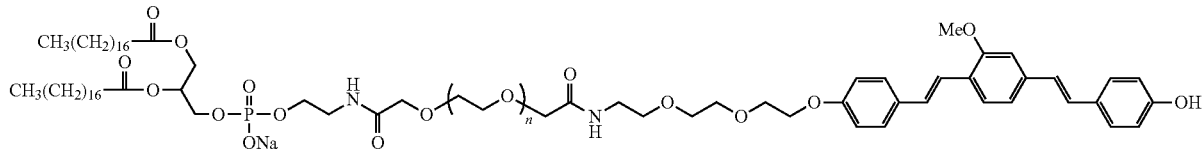

wherein n may be about 10 to about 100, about 30 to about 80, or about 30 to about 60.

In one embodiment, a phospholipid-polymer-aromatic compound conjugate is provided. The phospholipid-polymer-aromatic compound conjugate may be represented by PL-AL-PEG-aromatic compound, wherein PL may be a phospholipid, AL may be an aliphatic linkage, PEG may be a polyethylene glycol polymer, and the aromatic compound may be represented by one of Formulas I, II, III, IV, V, VI, and VII as described herein.

In one embodiment, a phospholipid-polymer-aromatic compound conjugate is provided. The phospholipid-polymer-aromatic compound conjugate may be represented by:

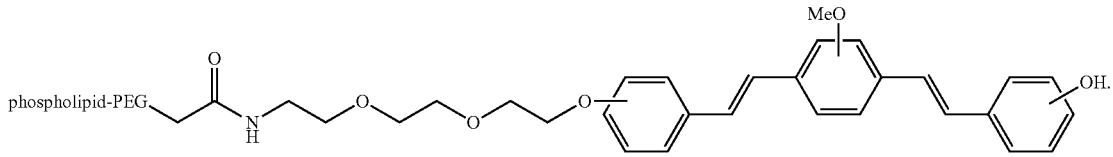

In some embodiments of the phospholipid-polymer-aromatic compound conjugate, AL may include one or more of: an amide linkage and a carbamate linkage.

In some embodiments of the phospholipid-polymer-aromatic compound conjugate, the phospholipid-polymer-aromatic compound conjugate may include a compound represented by:

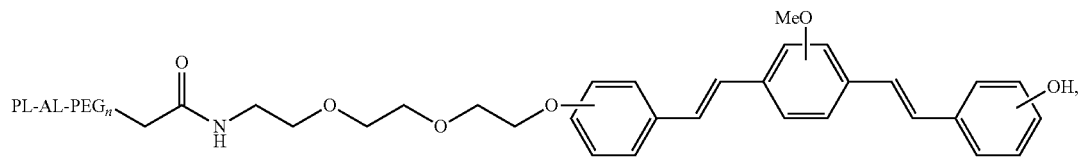

wherein n represents a degree of polymerization of the polyethylene glycol polymer, and may be about 10 to about 100, about 30 to about 80, or about 30 to about 60.

In some embodiments of the phospholipid-polymer-aromatic compound conjugate, the phospholipid-polymer-aromatic compound conjugate may include a compound represented by:

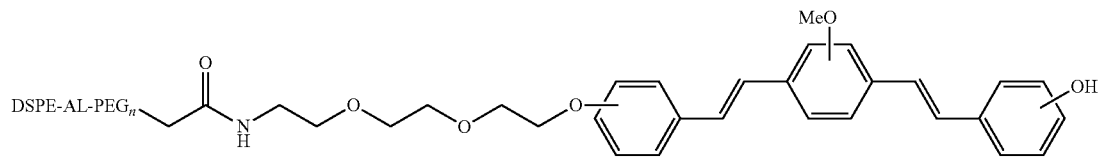

wherein n represents a degree of polymerization of the polyethylene glycol polymer, and may be about 10 to about 100, about 30 to about 80, or about 30 to about 60.

In several embodiments of the phospholipid-polymer-aromatic compound conjugate, the phospholipid-polymer-aromatic compound conjugate may include a compound represented by:

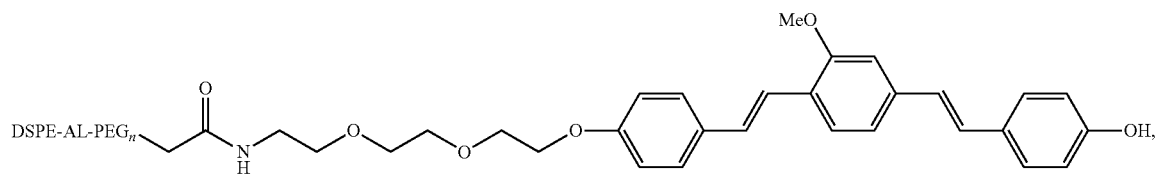

wherein n represents a degree of polymerization of the polyethylene glycol polymer, and may be about 10 to about 100, about 30 to about 80, or about 30 to about 60.

In various embodiments of the method, the phospholipid-polymer-aromatic compound conjugate may include a compound represented by one or more of:

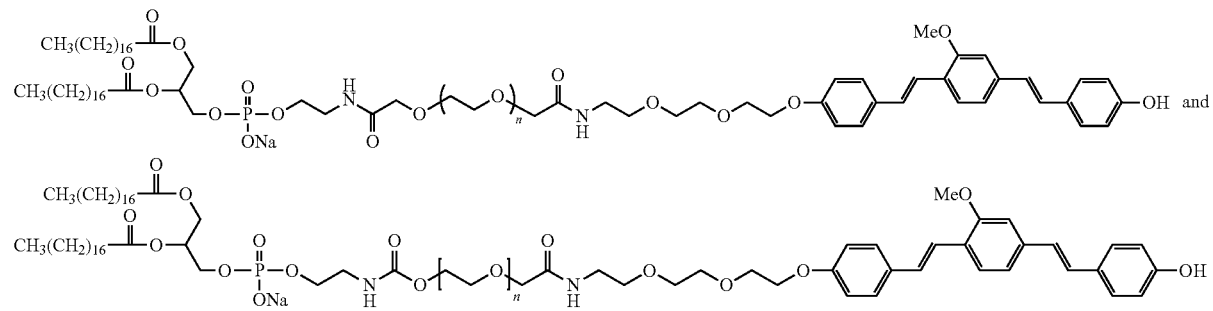

wherein n may be about 10 to about 100, about 30 to about 80, or about 30 to about 60.

In one embodiment, a compound of Formula I, or a pharmaceutically acceptable salt or prodrug thereof, is provided:

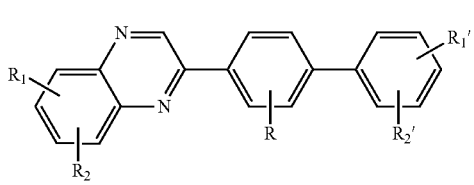

I wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula I may be conjugated with a hydrophilic polymer, e.g., polyethylene glycol ("PEG") and the like, and a phospholipid, e.g., 1,2-dipalmitoyl-sn-glycero-3-phosphocholine ("DPPC"), 1,2-distearoyl-sn-glycero-3-phosphoethanolamine ("DSPE"), 1,2-distearoyl-sn-glycero-3-phosphocholine ("DSPC"), 1,2-Dipalmitoyl-sn-glycero-3-phosphoethanolamine ("DPPE"), and the like, to form a phospholipid-hydrophilic polymer—Formula I ligand conjugate. In one embodiment, the phospholipid-hydrophilic polymer—Formula I ligand conjugate may be incorporated into a liposomal composition.

In one embodiment, a method for imaging amyloid deposits in a patient is provided, the method comprising:
 introducing into the patient a detectable quantity of a liposomal composition comprising a phospholipid-hydrophilic polymer—Formula I ligand conjugate;
 allowing sufficient time for the liposomal composition to be associated with one or more amyloid deposits; and
 detecting the liposomal composition associated with the one or more amyloid deposits.

In one embodiment, a compound of Formula II, or a pharmaceutically acceptable salt or prodrug thereof, is provided:

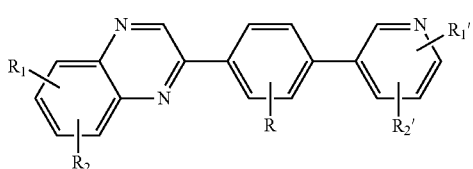

II wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula II may be conjugated with a hydrophilic polymer, e.g., PEG and the like, and a phospholipid, e.g., DPPC, DSPE, DSPC, DPPE, and the like, to form a phospholipid-hydrophilic polymer—Formula II ligand conjugate. In one embodiment, the phospholipid-hydrophilic polymer—Formula II ligand conjugate may be incorporated into a liposomal composition.

In one embodiment, a method for imaging amyloid deposits in a patient is provided, the method comprising:
 introducing into the patient a detectable quantity of a liposomal composition comprising a phospholipid-hydrophilic polymer—Formula II ligand conjugate;
 allowing sufficient time for the liposomal composition to be associated with one or more amyloid deposits; and
 detecting the liposomal composition associated with the one or more amyloid deposits.

In one embodiment, a compound of Formula III, or a pharmaceutically acceptable salt or prodrug thereof, is provided:

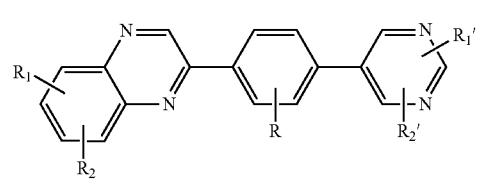

III wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula III may be conjugated with a hydrophilic polymer, e.g., PEG and the like, and a phospholipid, e.g., DPPC, DSPE, DSPC, DPPE, and the like, to form a phospholipid-hydrophilic polymer—Formula III ligand conjugate. In one embodiment, the phospholipid-hydrophilic polymer—Formula III ligand conjugate may be incorporated into a liposomal composition.

In one embodiment, a method for imaging amyloid deposits in a patient is provided, the method comprising:
 introducing into the patient a detectable quantity of a liposomal composition comprising a phospholipid-hydrophilic polymer—Formula III ligand conjugate;
 allowing sufficient time for the liposomal composition to be associated with one or more amyloid deposits; and
 detecting the liposomal composition associated with the one or more amyloid deposits.

In one embodiment, a compound of Formula IV, or a pharmaceutically acceptable salt or prodrug thereof, is provided:

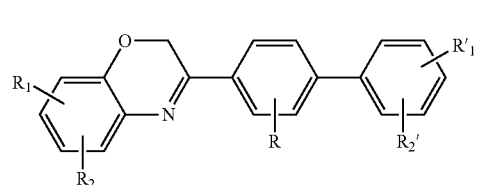

IV wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula IV may be conjugated with a hydrophilic polymer, e.g., PEG and the like, and a phospholipid, e.g., DPPC, DSPE, DSPC, DPPE, and the like, to form a phospholipid-hydrophilic polymer—Formula IV ligand conjugate. In one embodiment, the phospholipid-hydrophilic polymer—Formula IV ligand conjugate may be incorporated into a liposomal composition.

In one embodiment, a method for imaging amyloid deposits in a patient is provided, the method comprising:
 introducing into the patient a detectable quantity of a liposomal composition comprising a phospholipid-hydrophilic polymer—Formula IV ligand conjugate;
 allowing sufficient time for the liposomal composition to be associated with one or more amyloid deposits; and detecting the liposomal composition associated with the one or more amyloid deposits.

In one embodiment, a compound of Formula V, or a pharmaceutically acceptable salt or prodrug thereof, is provided:

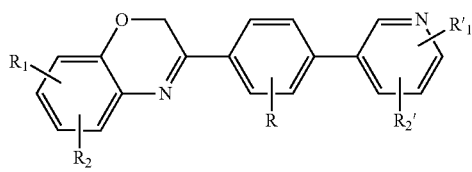

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula V may be conjugated with a hydrophilic polymer, e.g., PEG and the like, and a phospholipid, e.g., DPPC, DSPE, DSPC, DPPE, and the like, to form a phospholipid-hydrophilic polymer—Formula V ligand conjugate. In one embodiment, the phospholipid-hydrophilic polymer—Formula V ligand conjugate may be incorporated into a liposomal composition.

In one embodiment, a method for imaging amyloid deposits in a patient is provided, the method comprising:

introducing into the patient a detectable quantity of a liposomal composition comprising a phospholipid-hydrophilic polymer—Formula V ligand conjugate;

allowing sufficient time for the liposomal composition to be associated with one or more amyloid deposits; and detecting the liposomal composition associated with the one or more amyloid deposits.

In one embodiment, a compound of Formula VI, or a pharmaceutically acceptable salt or prodrug thereof, is provided:

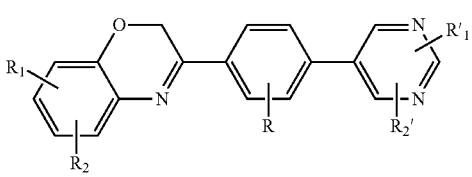

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula VI may be conjugated with a hydrophilic polymer, e.g., PEG and the like, and a phospholipid, e.g., DPPC, DSPE, DSPC, DPPE, and the like, to form a phospholipid-hydrophilic polymer—Formula VI ligand conjugate. In one embodiment, the phospholipid-hydrophilic polymer—Formula VI ligand conjugate may be incorporated into a liposomal composition.

In one embodiment, a method for imaging amyloid deposits in a patient is provided, the method comprising:

introducing into the patient a detectable quantity of a liposomal composition comprising a phospholipid-hydrophilic polymer—Formula VI ligand conjugate;

allowing sufficient time for the liposomal composition to be associated with one or more amyloid deposits; and detecting the liposomal composition associated with the one or more amyloid deposits.

In one embodiment, a compound of Formula VII, or a pharmaceutically acceptable salt or prodrug thereof, is provided:

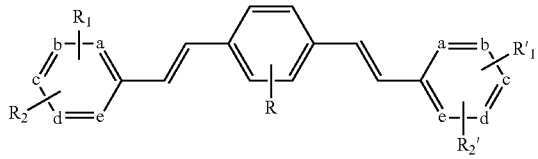

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl; and wherein a, b, c, d, e=C, N, O, or S.

In one embodiment, the aromatic compound of Formula VII may be conjugated with a hydrophilic polymer, e.g., PEG and the like, and a phospholipid, e.g., DPPC, DSPE, DSPC, DPPE, and the like, to form a phospholipid-hydrophilic polymer—Formula VII ligand conjugate. In one embodiment, the phospholipid-hydrophilic polymer—Formula VII ligand conjugate may be incorporated into a liposomal composition.

In one embodiment, a method for imaging amyloid deposits in a patient is provided, the method comprising:

introducing into the patient a detectable quantity of a liposomal composition comprising a phospholipid-hydrophilic polymer—Formula VII ligand conjugate;

allowing sufficient time for the liposomal composition to be associated with one or more amyloid deposits; and detecting the liposomal composition associated with the one or more amyloid deposits.

In one embodiment, a liposomal composition is provided, the liposomal composition comprising:

a phospholipid;

cholesterol, or another stabilizing excipient, such as another sterol or a fatty acid;

a nonradioactive gadolinium-containing contrast enhancing agent;

a phospholipid which is derivatized with a polymer; and a conjugate comprising an aromatic compound having any one of Formulas I-VII, such as a conjugate in a form of a phospholipid-hydrophilic polymer-aromatic conjugate as described herein.

In one embodiment, the liposomal composition comprises:

DPPC;

cholesterol;

(diethylenetriaminepentaacetic acid)-bis(stearylamide), gadolinium salt ("Gd-DTPA-BSA")

1,2-distearoyl-sn-glycero-3-phosphoethanolamine-N-[methoxy(polyethylene glycol)-2000] ("DSPE-mPEG-2000"; CAS No. 147867-65-0); and DSPE-AL-$PEG_n$-methoxy-XO4, where n represents a degree of polymerization of the polyethylene glycol polymer, and may be about 10 to about 100, about 30 to about 80, or about 30 to about 60.

In one embodiment, a method for imaging amyloid deposits in a patient is provided, the method comprising:

introducing into the patient a detectable quantity of a liposomal composition comprising a phospholipid; cholesterol, or another stabilizing excipient, such as another sterol or a fatty acid; a nonradioactive gadolinium-containing contrast enhancing agent; a phospholipid which is derivatized with a polymer; and a conjugate comprising an aromatic compound having any one of Formulas I-VII, such as a conjugate in a form of a phospholipid-hydrophilic polymer-aromatic compound conjugate as described herein;

allowing sufficient time for the liposomal composition to be associated with one or more amyloid deposits; and detecting the liposomal composition associated with the one or more amyloid deposits.

In one embodiment, the detecting comprises detecting by fluorescence imaging (FI). In another embodiment, the detecting comprises detecting by magnetic resonance imaging (MRI). In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, the detecting comprises detecting by FI. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula I, or a pharmaceutically acceptable salt or prodrug thereof, is provided:

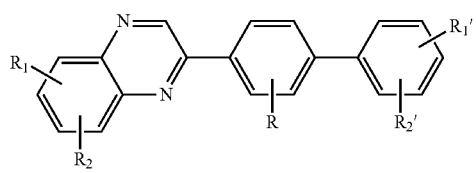

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=H, $R_2$=H, and $R_1'$ and $R_2'$ together form the linkage —O—$CH_2$—O— to form a 1,3-benzodioxole. Thus, one example of a compound of Formula I is the 1,4-quinoxaline phenyl 1,3-benzodioxolyl compound IA:

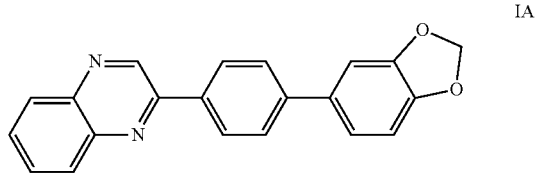 [SMILES: c1ccc2nc(-c3ccc(-c4ccc5c(c4)OCO5)cc3)cnc2c1]

In another embodiment, R=H, $R_1$=H, $R_2$=H, $R_1'$=H, and $R_2'$=$NMe_2$. Thus, another example of a compound of Formula I is the 1,4-quinoxaline biphenyl compound IB:

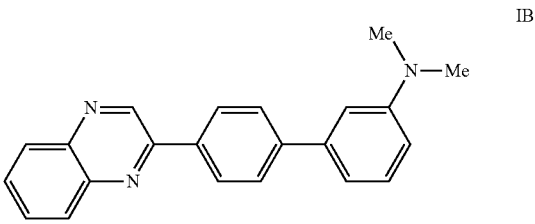 [SMILES: CN(C)c1cccc(-c2ccc(-c3cnc4ccccc4n3)cc2)c1]

In one embodiment, the aromatic heterocycle of Formula I may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer—Formula I ligand conjugate.

In one embodiment, the phospholipid-hydrophilic polymer—Formula I ligand conjugate comprises a compound represented by:

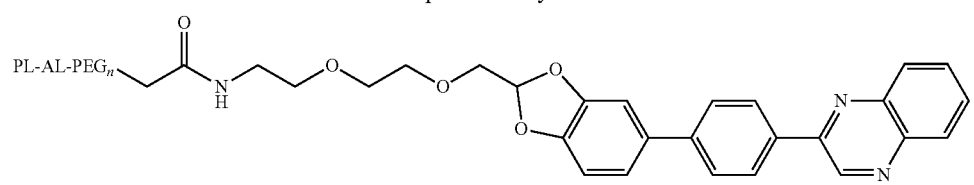

e.g., one or more of:

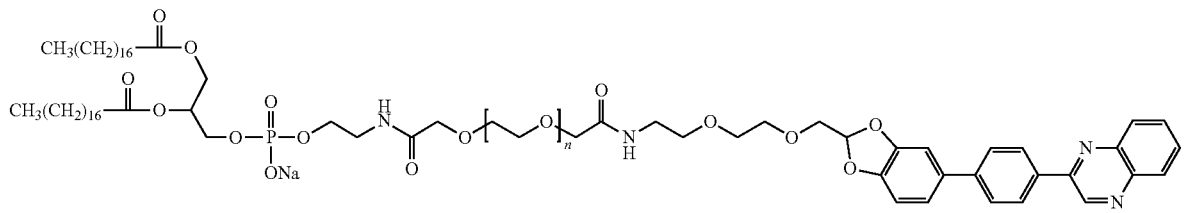

and

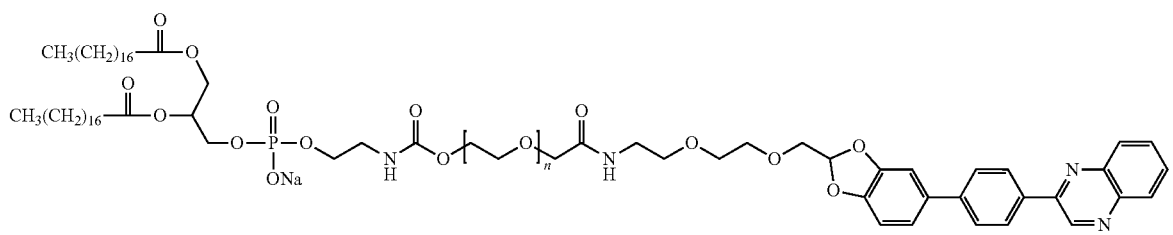

wherein n may be about 10 to about 100, about 30 to about 80, or about 30 to about 60.

In another embodiment, the phospholipid-hydrophilic polymer—Formula I ligand conjugate comprises a compound represented by:

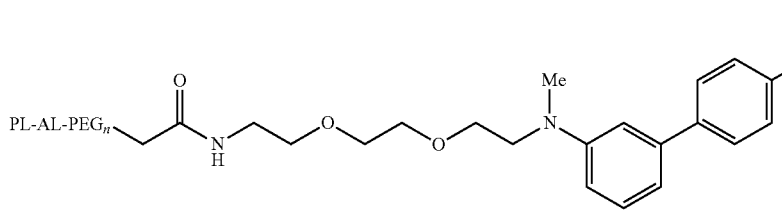

e.g., one or more of:

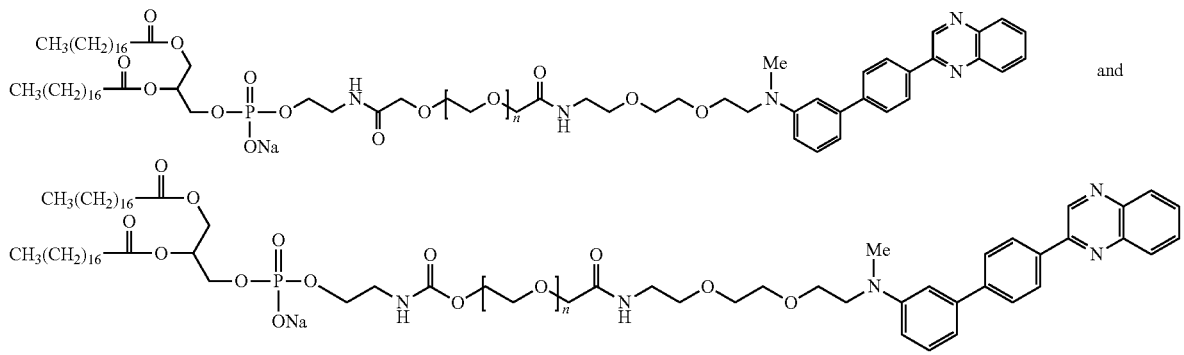

wherein n may be about 10 to about 100, about 30 to about 80, or about 30 to about 60.

In one embodiment, the phospholipid-hydrophilic polymer—Formula I ligand conjugate may be incorporated into a liposomal composition.

In one embodiment, a method for imaging amyloid deposits in a patient is provided, the method comprising:

introducing into the patient a detectable quantity of a liposomal composition comprising a phospholipid-hydrophilic polymer—Formula I ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula II, or a pharmaceutically acceptable salt or prodrug thereof, is provided:

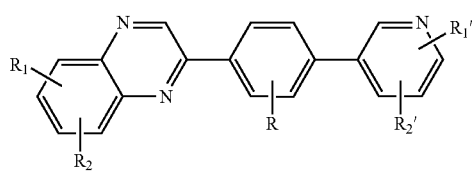

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=H, $R_2$=H, $R_1'$=H, and $R_2'$=OMe. Thus, one example of a compound of Formula II is the 1,4-quinoxaline phenyl pyridinyl compound IIA:

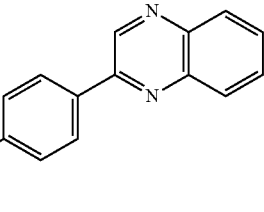

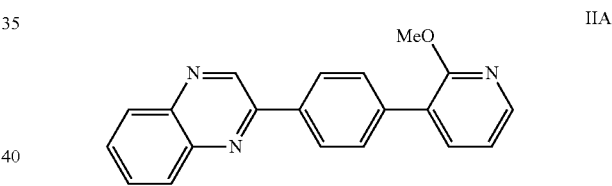

IIA

Another example of a compound of Formula II is the 1,4-quinoxaline phenyl pyridinyl compound IIB:

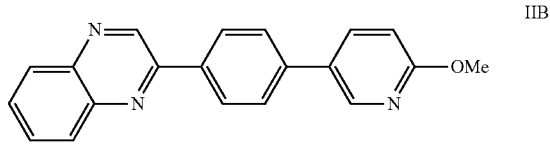 [SMILES: COc1ccc(-c2ccc(-c3cnc4ccccc4n3)cc2)cn1]

IIB

In one embodiment, the aromatic heterocycle of Formula II may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer—Formula II ligand conjugate.

In one embodiment, the phospholipid-hydrophilic polymer—Formula II ligand conjugate comprises a compound represented by:

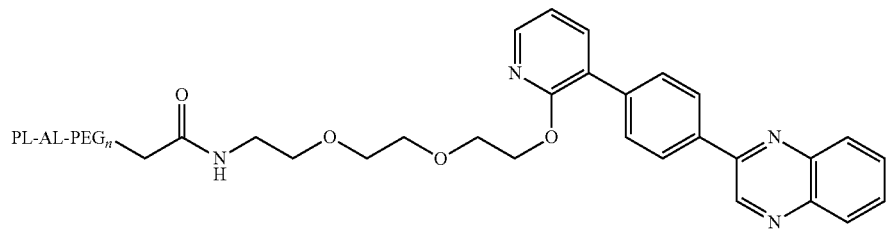

e.g., one or more of:

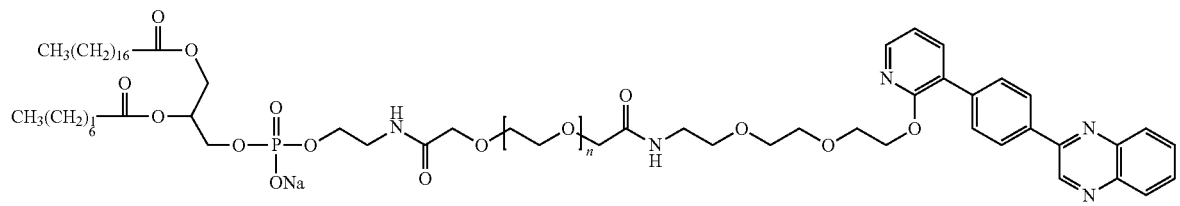

and

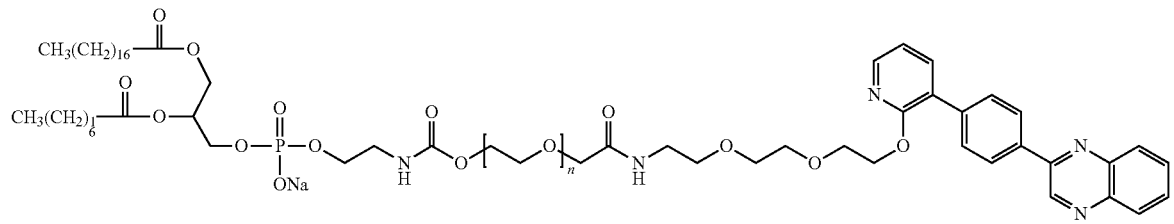

wherein n may be about 10 to about 100, about 30 to about 80, or about 30 to about 60.

In another embodiment, the phospholipid-hydrophilic polymer—Formula II ligand conjugate comprises a compound represented by:

wherein n may be about 10 to about 100, about 30 to about 80, or about 30 to about 60.

In one embodiment, the phospholipid-hydrophilic polymer—Formula II ligand conjugate may be incorporated into a liposomal composition.

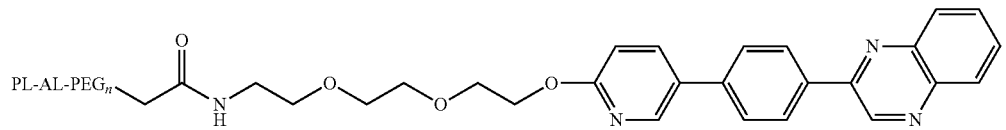

e.g., one or more of:

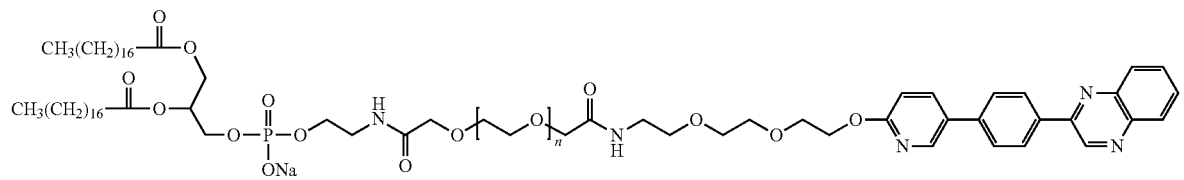

and

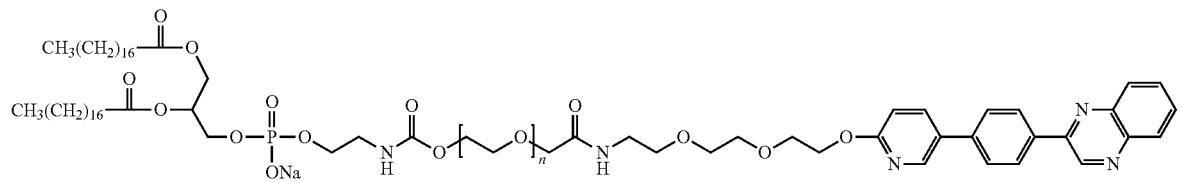

In one embodiment, a method for imaging amyloid deposits in a patient is provided, the method comprising:

introducing into the patient a detectable quantity of a liposomal composition comprising a phospholipid-hydrophilic polymer—Formula II ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula III, or a pharmaceutically acceptable salt or prodrug thereof, is provided:

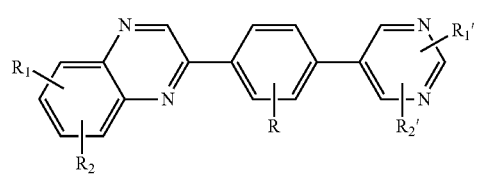

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=H, $R_2$=H, $R_1'$=OMe, and $R_2'$=OMe. Thus, one example of a compound of Formula III is the 1,4-quinoxaline phenyl pyrimidinyl compound IIIA:

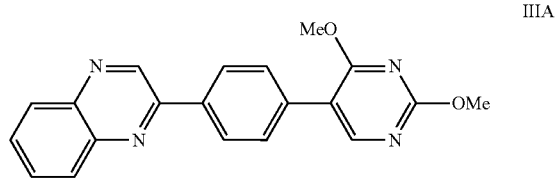 [SMILES: COc1ncc(-c2ccc(-c3cnc4ccccc4n3)cc2)c(OC)n1]

In one embodiment, the aromatic heterocycle of Formula III may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer—Formula III ligand conjugate.

In one embodiment, the phospholipid-hydrophilic polymer—Formula III ligand conjugate comprises a compound represented by:

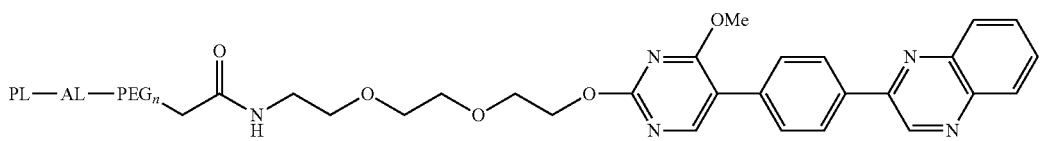

e.g., one or more of:

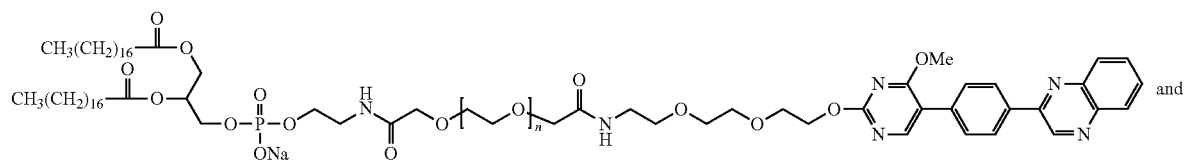

and

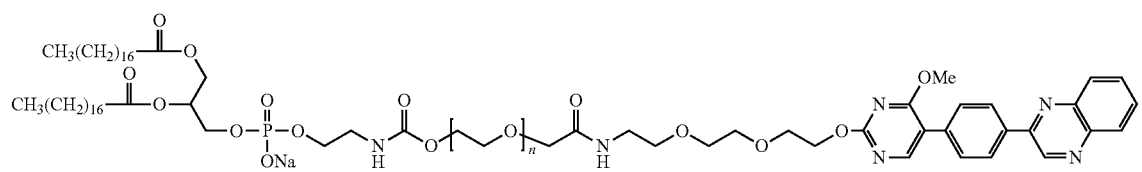

wherein n may be about 10 to about 100, about 30 to about 80, or about 30 to about 60.

In one embodiment, the phospholipid-hydrophilic polymer—Formula III ligand conjugate may be incorporated into a liposomal composition.

In one embodiment, a method for imaging amyloid deposit in a patient is provided, the method comprising:

introducing into the patient a detectable quantity of a liposomal composition comprising a phospholipid-hydrophilic polymer—Formula III ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula IV, or a pharmaceutically acceptable salt or prodrug thereof, is provided:

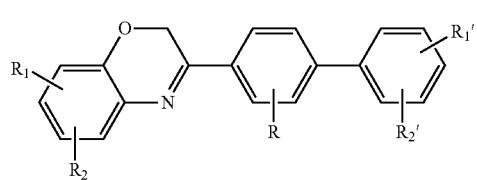

IV wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=Me, $R_2$=H, and $R_1'$ and $R_2'$ together form the linkage —O—$CH_2$—O— to form a 1,3-benzodioxole. Thus, one example of a compound of Formula IV is the 1,4-benzoxazine phenyl 1,3-benzodioxolyl compound IVA:

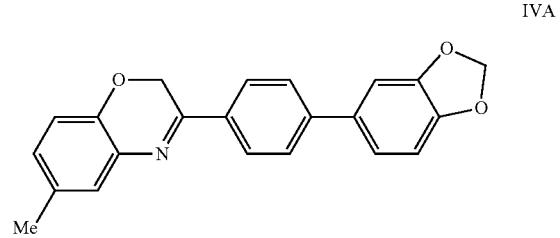 [SMILES: Cc1ccc2c(c1)N=C(c1ccc(-c3ccc4c(c3)OCO4)cc1)CO2]

IVA

In another embodiment, R=H, $R_1$=Me, $R_2$=H, $R_1'$=H, and $R_2'$=$NMe_2$. Thus, another example of a compound of Formula IV is the 1,4-benzoxazine biphenyl compound IVB:

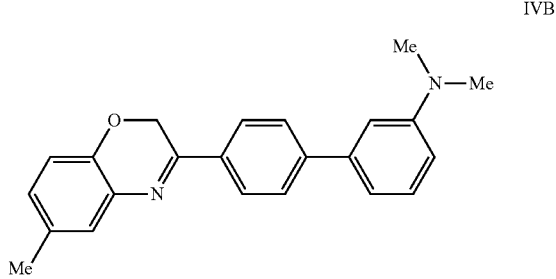 [SMILES: Cc1ccc2c(c1)N=C(c1ccc(-c3cccc(N(C)C)c3)cc1)CO2]

IVB

In one embodiment, the aromatic heterocycle of Formula IV may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer—Formula IV ligand conjugate.

In one embodiment, the phospholipid-hydrophilic polymer—Formula IV ligand conjugate comprises a compound represented by:

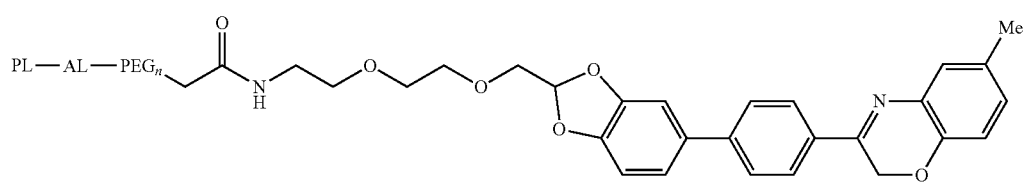

e.g., one or more of:

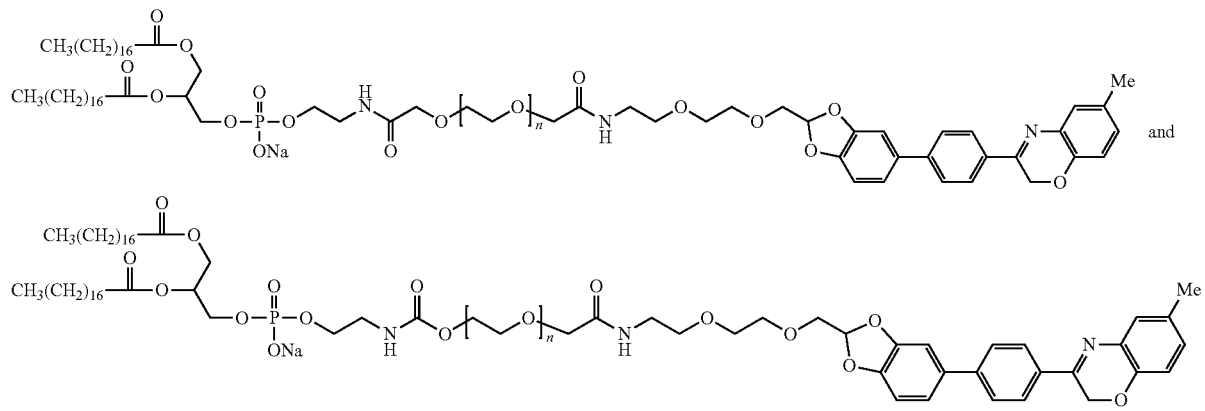

wherein n may be about 10 to about 100, about 30 to about 80, or about 30 to about 60.

In another embodiment, the phospholipid-hydrophilic polymer—Formula IV ligand conjugate comprises a compound represented by:

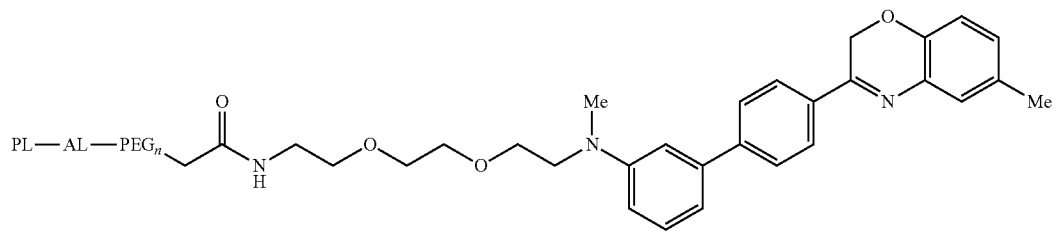

e.g., one or more of:

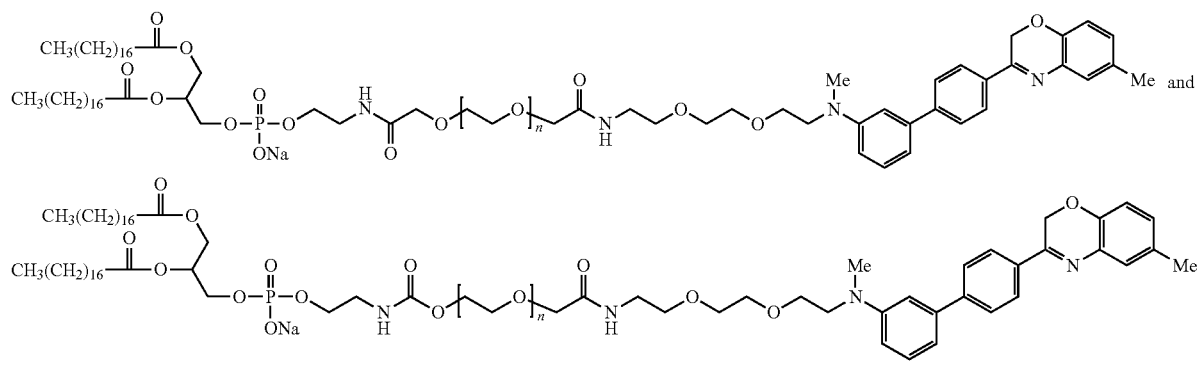

wherein n may be about 10 to about 100, about 30 to about 80, or about 30 to about 60.

In one embodiment, the phospholipid-hydrophilic polymer—Formula IV ligand conjugate may be incorporated into a liposomal composition.

In one embodiment, a method for imaging amyloid deposits in a patient is provided, the method comprising:

introducing into the patient a detectable quantity of a liposomal composition comprising a phospholipid-hydrophilic polymer—Formula IV ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula V, or a pharmaceutically acceptable salt or prodrug thereof, is provided:

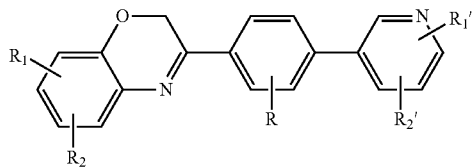

V wherein R, R$_1$, R$_2$, R$_1$', R$_2$'=H, F, Cl, Br, I, alkyl, aryl, OH, O-alkyl, O-aryl, NH$_2$, NH-alkyl, N-dialkyl, carboxyl, sulfonyl, carbamoyl, or glycosyl.

In one embodiment, R=H, R$_1$=Me, R$_2$=H, R$_1$'=H, and R$_2$'=OMe. Thus, one example of a compound of Formula V is the 1,4-benzoxazine phenyl pyridinyl compound VA:

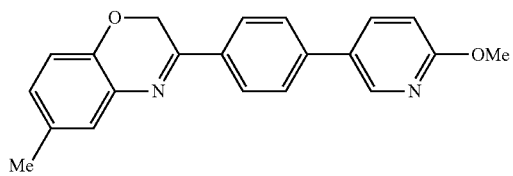

VA

In one embodiment, the aromatic heterocycle of Formula V may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer—Formula V ligand conjugate.

In one embodiment, the phospholipid-hydrophilic polymer—Formula V ligand conjugate comprises a compound represented by:

wherein n may be about 10 to about 100, about 30 to about 80, or about 30 to about 60.

In one embodiment, the phospholipid-hydrophilic polymer—Formula V ligand conjugate may be incorporated into a liposomal composition.

In one embodiment, a method for imaging amyloid deposits in a patient is provided, the method comprising:
introducing into the patient a detectable quantity of a liposomal composition comprising a phospholipid-hydrophilic polymer—Formula V ligand conjugate;
allowing sufficient time for the liposomal composition to be associated with one or more amyloid deposits; and
detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula VI, or a pharmaceutically acceptable salt or prodrug thereof, is provided:

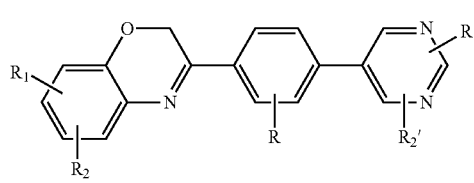

VI wherein R, R$_1$, R$_2$, R$_1$', R$_2$'=H, F, Cl, Br, I, alkyl, aryl, OH, O-alkyl, O-aryl, NH$_2$, NH-alkyl, N-dialkyl, carboxyl, sulfonyl, carbamoyl, or glycosyl.

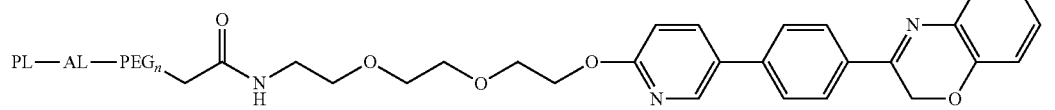

e.g., one or more of:

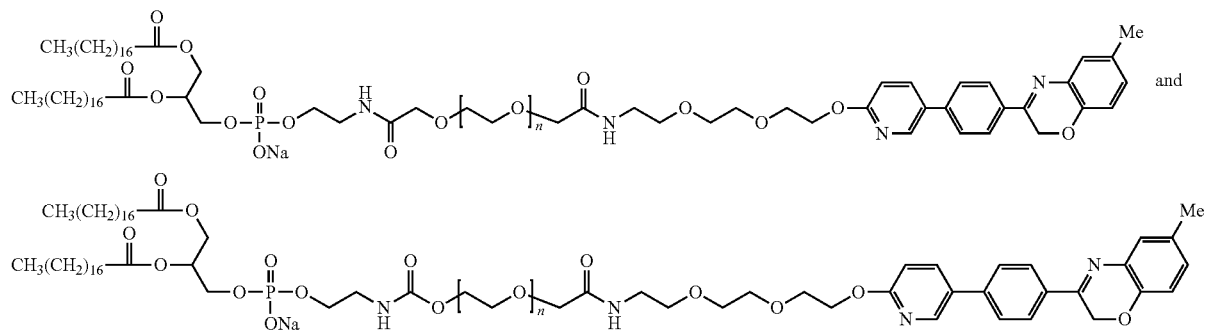

In one embodiment, R=H, R₁=Me, R₂=H, R₁'=OMe, and R₂'=OMe. Thus, one example of a compound of Formula VI is the 1,4-quinoxaline phenyl pyrimidinyl compound VIA:

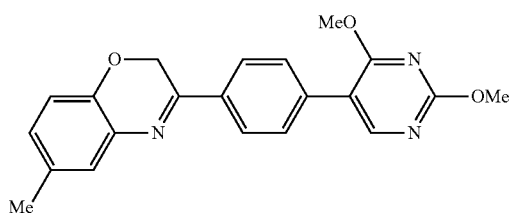

VIA

In one embodiment, the aromatic heterocycle of Formula VI may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer—Formula VI ligand conjugate.

In one embodiment, the phospholipid-hydrophilic polymer—Formula VI ligand conjugate comprises a compound represented by:

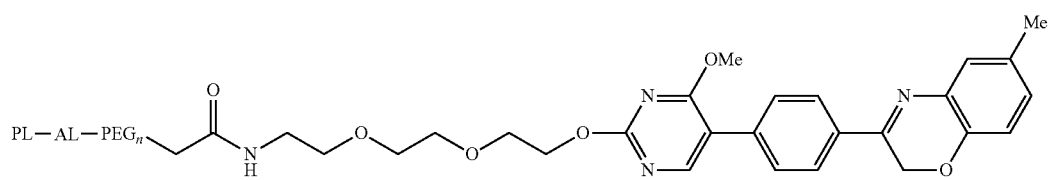

e.g., one or more of:

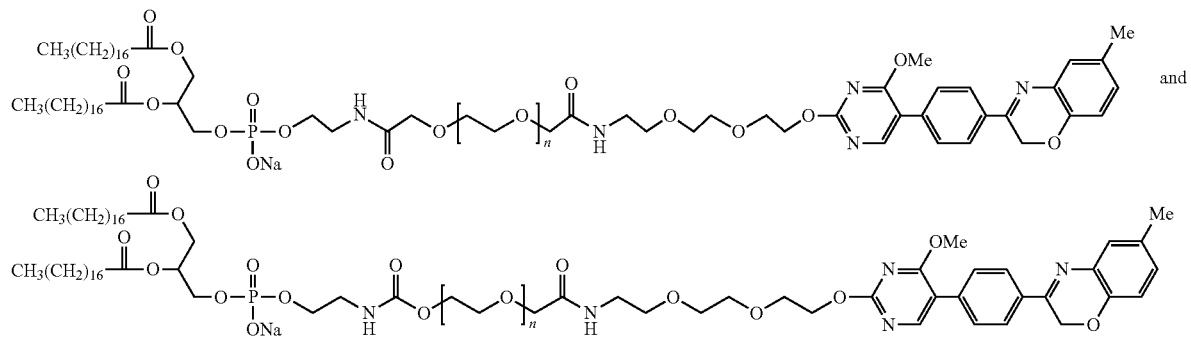

and wherein n may be about 10 to about 100, about 30 to about 80, or about 30 to about 60.

In one embodiment, the phospholipid-hydrophilic polymer—Formula VI ligand conjugate may be incorporated into a liposomal composition.

In one embodiment, a method for imaging amyloid deposits in a patient is provided, the method comprising:
  introducing into the patient a detectable quantity of a liposomal composition comprising a phospholipid-hydrophilic polymer—Formula VI ligand conjugate;
  allowing sufficient time for the liposomal composition to be associated with one or more amyloid deposits; and
  detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula VII, or a pharmaceutically acceptable salt or prodrug thereof, is provided:

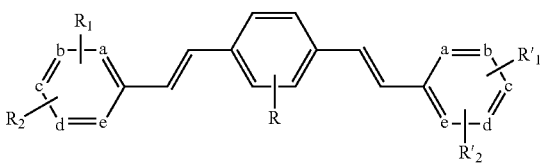

VII wherein R, R₁, R₂, R₁', R₂'=H, F, Cl, Br, I, alkyl, aryl, OH, O-alkyl, O-aryl, NH₂, NH-alkyl, N-dialkyl, carboxyl, sulfonyl, carbamoyl, or glycosyl, and a, b, c, d, e=C, N, O, or S.

In one embodiment, R=OMe, R₁=H, R₂=O-alkyl, R₁'=OH, and R₂'=H. Thus, one example of a compound of Formula VII is the divinyl benzene compound VIIA ("methoxy-XO4"):

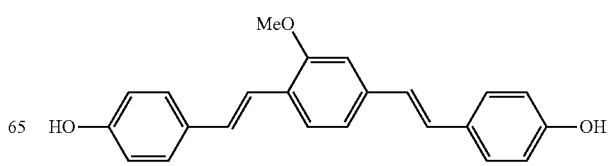

VIIA

In one embodiment, the aromatic compound of Formula VII may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer—Formula VII ligand conjugate represented by:

In one embodiment, the phospholipid-hydrophilic polymer—Formula VII ligand conjugate, e.g., Me-XO4, and even more particularly, DPSE-AL-PEG$_{3400}$-Methoxy-XO4 (where 3400 signifies the molecular weight of the polyethylene glycol), may be incorporated into a liposomal composition.

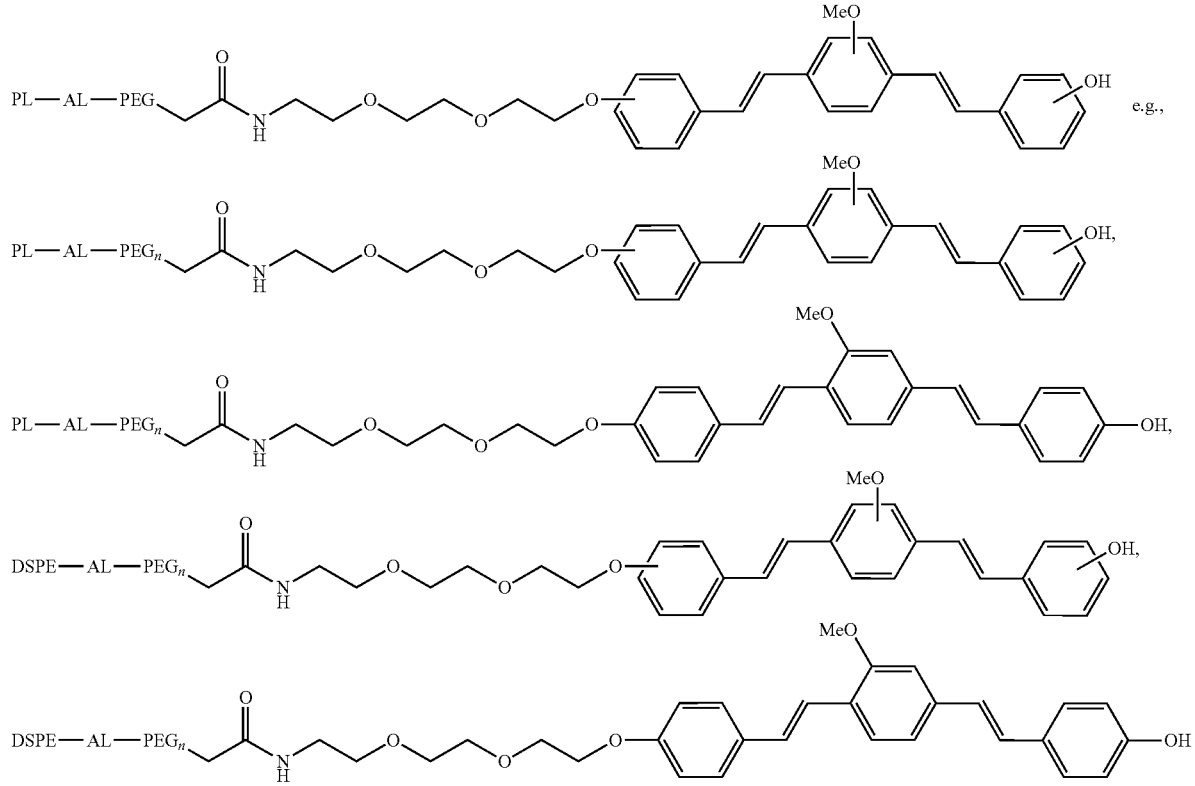

wherein n represents a degree of polymerization of the polyethylene glycol polymer, and may be about 10 to about 100, about 30 to about 80, or about 30 to about 60.

For example, in one embodiment, the methoxy-XO4 ligand may be conjugated with PEG and DSPE to form the DSPE-AL-PEG$_n$-Methoxy-XO4 conjugate shown as "1" in FIG. 1 (and sometimes referred to hereinafter as "Me-XO4"), which includes one or more of:

In one embodiment, a method for imaging amyloid deposits in a patient is provided, the method comprising:

introducing into the patient a detectable quantity of a liposomal composition comprising a phospholipid-hydrophilic polymer—Formula VII ligand conjugate;

allowing sufficient time for the liposomal composition to be associated with one or more amyloid deposits; and

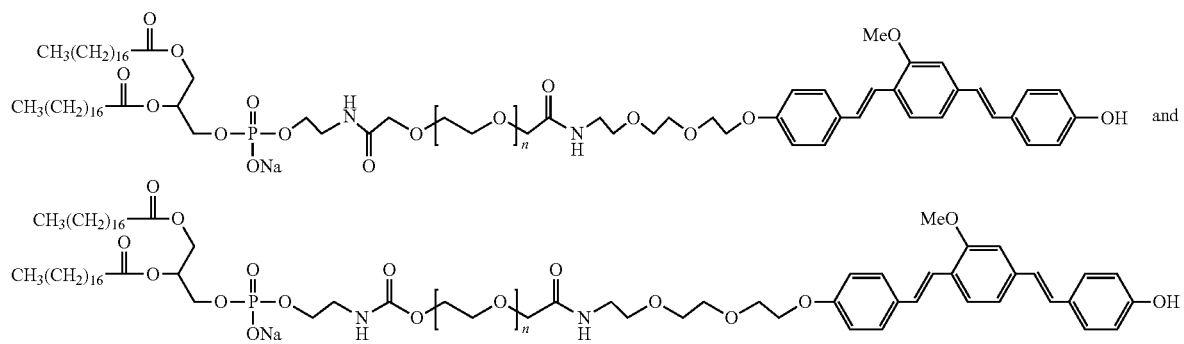

wherein n may be about 10 to about 100, about 30 to about 80, or about 30 to about 60.

detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, one or more alternative amyloid ligands (i.e., other than the amyloid binding ligands disclosed above), including, but not limited to, Congo red and its derivatives, Thioflavin T and its derivatives, and CG and its derivatives, may be conjugated with a hydrophilic polymer, e.g., PEG (having, e.g., a molecular weight ranging from 500-10,000 Da) and the like, and a phospholipid, e.g., DPPC, DSPE, DSPC, DPPE, and the like, to form a phospholipid-hydrophilic polymer-amyloid ligand conjugate. In one embodiment, the phospholipid-hydrophilic polymer-amyloid ligand conjugate may be incorporated into a liposomal composition.

In one embodiment, a method for imaging amyloid lesions in a patient is provided, the method comprising:
introducing into the patient a detectable quantity of a liposomal composition comprising a phospholipid-hydrophilic polymer-amyloid ligand conjugate;
allowing sufficient time for the liposomal composition to be associated with one or more amyloid deposits; and
detecting the liposomal composition associated with the one or more amyloid deposits.

The liposomal compositions described herein may further enable delivery of therapeutic molecules to amyloid lesions, thus enabling treatment of the lesions.

In one embodiment, a liposomal composition is provided, the liposomal composition comprising: a phospholipid; cholesterol, or another stabilizing excipient, such as another sterol or a fatty acid; a nonradioactive gadolinium-containing contrast enhancing agent; a phospholipid which is derivatized with a polymer; and a conjugate comprising an aromatic compound having any one of Formulas I-VII, such as a conjugate in a form of a phospholipid-hydrophilic polymer-aromatic conjugate as described herein.

In one embodiment, the liposomal composition comprises: DPPC; cholesterol; Gd-DTPA-BSA; DSPE-AL-mPEG-2000; and DSPE-AL-PEG$_n$-methoxy-XO4, where n represents a degree of polymerization of the polyethylene glycol polymer, and may be about 10 to about 100, about 30 to about 80, or about 30 to about 60.

In one embodiment, a method for imaging amyloid deposits in a patient is provided, the method comprising:
introducing into the patient a detectable quantity of a liposomal composition comprising a phospholipid; cholesterol, or another stabilizing excipient, such as another sterol or a fatty acid; a nonradioactive gadolinium-containing contrast enhancing agent; a phospholipid which is derivatized with a polymer; and a conjugate comprising an aromatic compound having any one of Formulas I-VII, such as a conjugate in a form of a phospholipid-hydrophilic polymer-aromatic compound conjugate as described herein;
allowing sufficient time for the liposomal composition to be associated with one or more amyloid deposits; and
detecting the liposomal composition associated with the one or more amyloid deposits.

In one embodiment, the detecting comprises detecting by FI. In another embodiment, the detecting comprises detecting by MRI. Indeed, hydrophilic paramagnetic chelates such as GdDTPA, GdDOTA, GdHPDO3A, GdDTPA-BMA, and GdDTPA-BSA are known MRI contrast agents. See U.S. Pat. No. 5,676,928 issued to Klaveness et al., which is incorporated by reference herein in its entirety. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

Suitable phospholipids may include those disclosed herein, and may further include those disclosed in U.S. Pat. No. 7,785,568 issued to Annapragada et al., which is incorporated by reference herein in its entirety. Suitable polymer derivatized phospholipids may include those disclosed herein, and may further include those disclosed in U.S. Pat. No. 7,785,568.

In one embodiment, the detecting comprises detecting by FI. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD"). Any other suitable type of imaging methodology known by those skilled in the art is contemplated, including, but not limited to, PET imaging.

EXAMPLES

Certain embodiments are described below in the form of examples. It is impossible to depict every potential application of the invention. Thus, while the embodiments are described in considerable detail, it is not the intention to restrict or in any way limit the scope of the appended claims to such detail, or to any particular embodiment.

Example 1: Preparation of DSPE-AL-PEG$_{3400}$-Methoxy-XO4 Conjugate 1

The DSPE-AL-PEG$_{MW=3400}$-Methoxy-XO4 conjugate, 1, was synthesized as the targeting species (FIG. 1) and later incorporated into liposomal formulations.

Referring to FIG. 1, the synthesis of compound 14 was achieved via a series of Takai, Suzuki, and Julia-Kocienski olefination reactions. The Boc-protected 3-unit PEG linker precursor bromide 3 was prepared from the corresponding commercially available alcohol 2 in good yield. Intermediate 7, the sulfone for the Julia-Kocienski olefination step was also prepared in excellent yields from 4-hydroxybenzaldehyde. 4-hydroxybenzaldehyde was also separately subjected to the standard Takai protocol to afford vinyl iodide 9. Reaction of 9 with commercially available boronic acid 10 under Suzuki conditions afforded compound 11 in good yield. The linker moiety was installed quantitatively to give aldehyde 12, which was exposed to sulfone 7 under optimized Julia-Kocienski conditions to obtain the desired E,E-isomer 13 in 69% yield after column chromatography purification. Global deprotection of the MOM and Boc groups with HCl gave the 14 as the hydrochloride salt.

Conjugation to the phospholipid-AL-PEG moiety proceeded by subjecting 14 and DSPE-AL-PEG$_{MW=3400}$-COOH to standard carbodiimide conditions to afford the DSPE-AL-PEG$_{MW=3400}$-MeXO4 conjugate 1 (a subset of Me-XO4).

Commercial sources of linkers such as "DSPE-PEG-COOH" and "DSPE-PEG-NH$_2$" include, for example, Biochempeg Scientific Inc., Watertown, Mass., and Laysan Bio, Arab, Ala. In catalog descriptions, such linkers are shown with structures depicting specific aliphatic linkages between the phospholipid and PEG moieties. During an initial series of experiments, the catalog structures for PL-AL-PEG linkers provided by such commercial sources were assumed correct, as well as catalog structures for commercially available PL-AL-PEG-NH$_2$ and PL-AL-PEG-CO$_2$H compounds used in constructing the liposomes described herein. It was subsequently found that PL-AL-PEG linkers compounds between different commercial sources, and even different lots from the same commercial source had AL including carbamate, AL including amide, a mixture of compounds with AL as carbamate or amide, and the like. After further investigation, it was determined that the results described herein for liposome formation and subsequent imaging using PL-AL-PEG linkers and PL-AL-PEG compounds were similar regardless of whether the aliphatic linkage AL included a carbamate, an amide, or mixtures of such compounds.

Figure 1A:
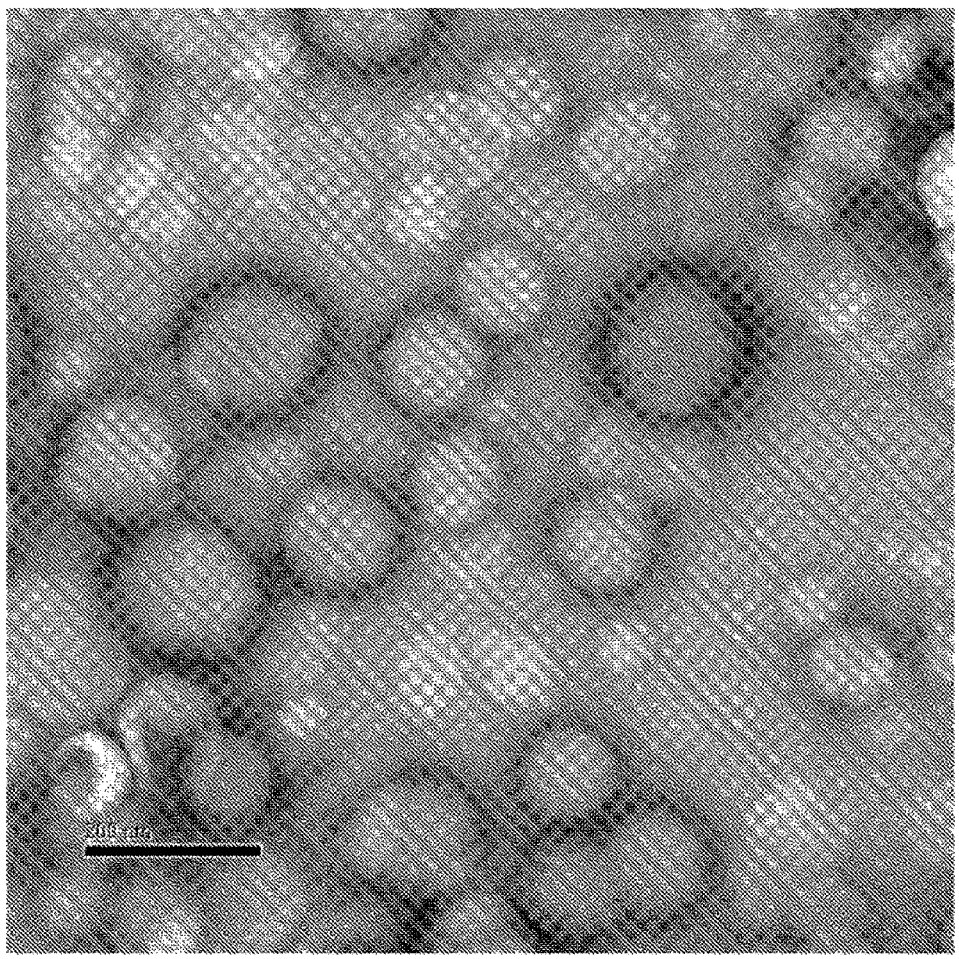
FIG. 1A illustrates example transmission electron microscope ("TEM") images of liposomal DSPE-AL-PEG$_{MW=3400}$-methoxy-XO4.
Figure 1B:
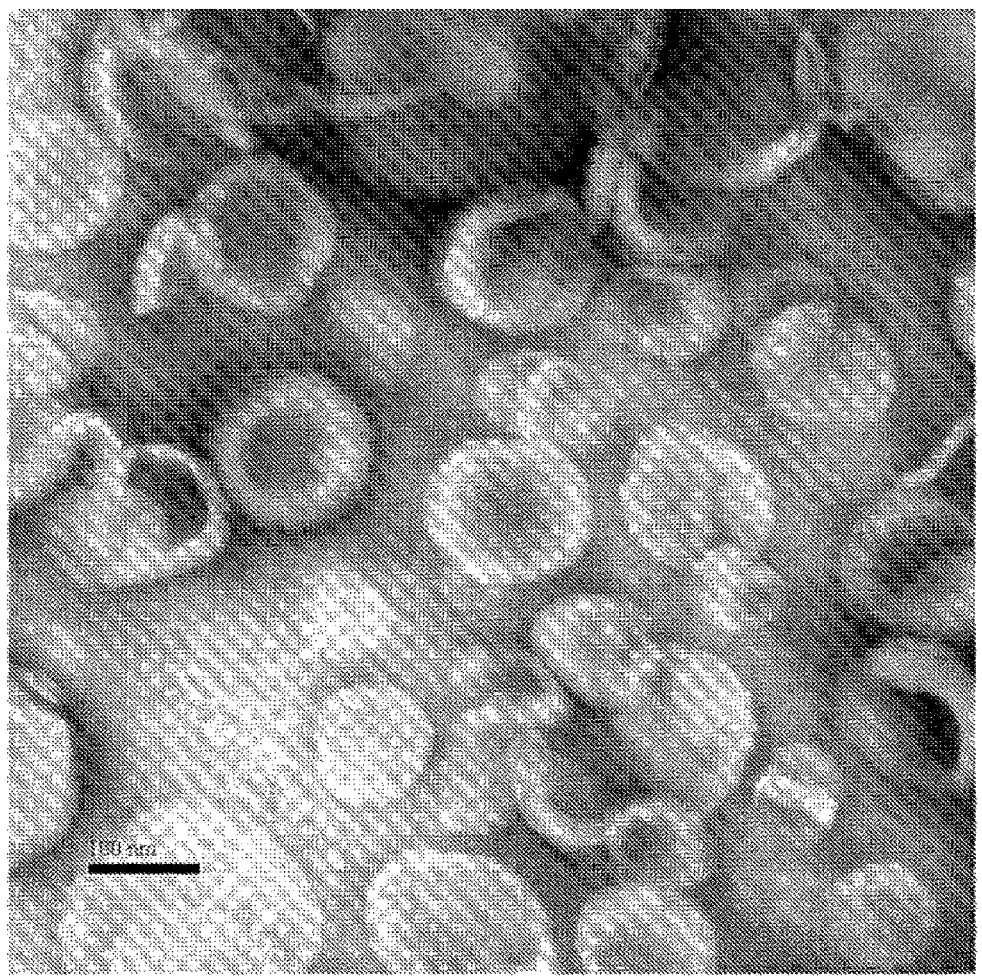
FIG. 1B illustrates further example TEM images of liposomal DSPE-AL-PEG$_{MW=3400}$-methoxy-XO4.

Example 2: Preparation and Characterization of Gd-Containing Me-XO4-Labeled Liposomes A lipid mixture (50 mM) comprising DPPC, cholesterol, Gd-DTPA-BSA, DSPE-AL-mPEG-2000, Me-XO4, and Rhodamine-DHPE (for optical detection) in about a 32.4:40:25:2:0.5:0.1 molar ratio, respectively, was employed. Other ratios are contemplated, including a lipid mixture comprising DPPC, cholesterol, Gd-DTPA-BSA, DSPE-AL-mPEG-2000, and Me-XO4 in about a 32.5:40:25:2:0.5 molar ratio. Additionally, the DSPE-AL-mPEG-2000 may be replaced altogether with the Me-XO4 conjugate, for a DPPC, cholesterol, Gd-DTPA-BSA, Me-XO4 conjugate ratio of 32.5:40:25:2.5. The upper limit on the PEG-bearing molecule may be about 15-25%, and the lower limit on cholesterol may be about 15-20%. Upon hydration in PROHANCE® solution (Bracco Diagnostics, Inc., Monroe Township, N.J.) for 1.5 h, the mixture was sequentially extruded, at 65° C., on a LIPEX™ THERMOLINE EXTRUDER (Northern Lipids Inc., Burnaby, B.C. Canada) with five passes through a 200 nm NUCLEPORE™ membrane (Sigma-Aldrich, St. Louis, Mo.) and ten passes through a 100 nm membrane. Particle size distribution was determined by TEM (FIGS. 1A and 1B), thereby confirming a mean diameter of about 100.8 nm and PDI of about 0.05.

The concentration of Me-XO4 ligand in the particles was determined using a fluorescence standard curve generated for Me-XO4 ligand to be 26 μM. The above protocol results in roughly equal distribution of the targeting ligand between the inner and the outer faces of the lipid bilayer. This implies that for each reported concentration of Me-XO4 ligand in the nanoparticles, approximately 50% of the total Me-XO4 ligands are available for binding. Me-XO4 ligand is highly intrinsically fluorescent and so are the nanoparticles bearing Me-XO4 ligand. This property was used as a reporter on the locations of nanoparticles in the course of all of the experiments.

Example 3: In Vitro Binding Affinity of Gd-Containing Me-XO4-Labeled Liposomes for Synthetic Aβ Fibrils The Me-XO4-labeled liposomes of Example 2 and Me-XO4 ligand stock solutions were diluted with 10 mM Tris-HCl, pH 7.4, to 500 nM. A small volume of the 100 μM Aβ stock solution was added to the test compounds to achieve a final fibril concentration of 20 μM. This was followed by addition of appropriate concentrations of the non-fluorescent competitor, CG. The binding mixture was incubated at RT for 1 h and then centrifuged for 20 min at 16,400 rpm to separate the fibrils. The precipitate was washed twice with tris-HCl. The fluorescence was measured in a SpectraMax 384 plate (Molecular Devices, Inc., Sunnyvale, Calif.) reader, using excitation and emission wavelengths of 368 nm and 450 nm, respectively.

Figure 2A:
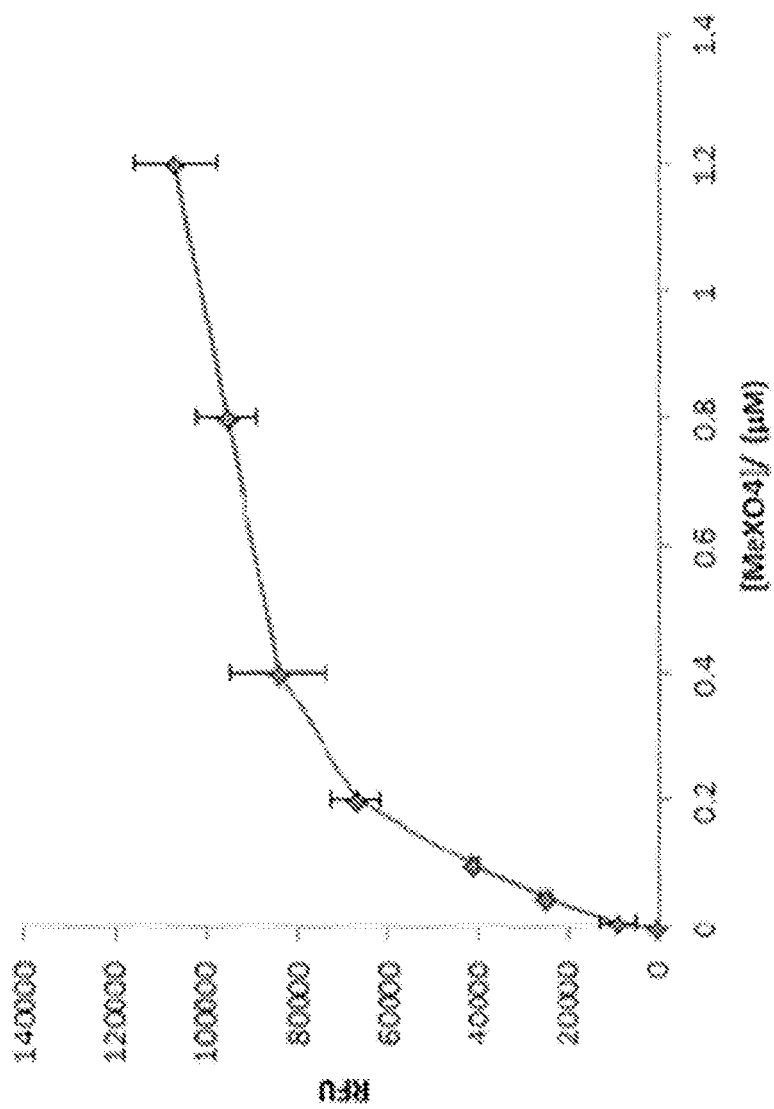
FIG. 2A illustrates the binding affinity of Me-XO4-labeled liposomes to synthetic Aβ (1-40) fibrils.
Figure 2B:
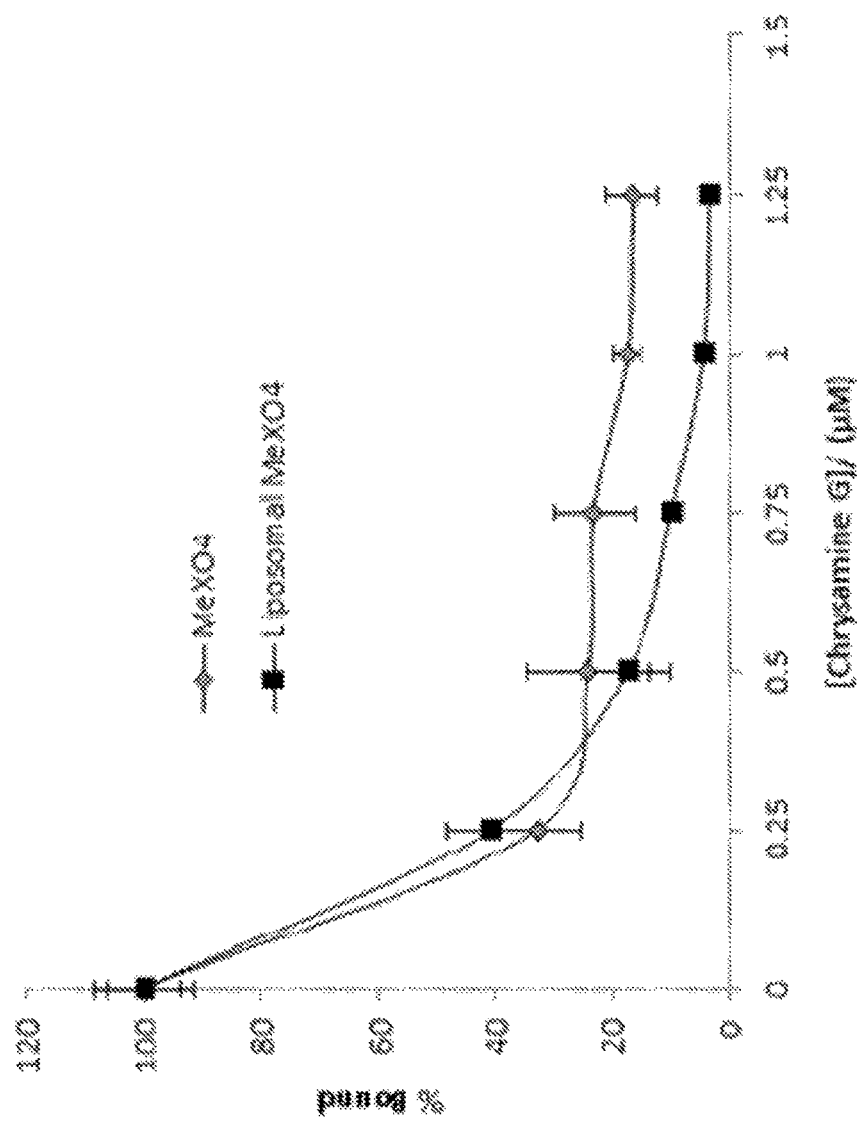
FIG. 2B illustrates example results of the competition between Me-XO4-labeled liposomes, Chrysamine G ("CG"), and free methoxy-XO4 ligand, for binding sites on synthetic Aβ (1-40) fibrils.

FIG. 2A illustrates the binding affinity of the Gd-containing Me-XO4-labeled liposomes of Example 2 to synthetic Aβ (1-40) aggregates. FIG. 2B illustrates the ability of Gd-containing Me-XO4-labeled liposomes to compete for binding sites with free Me-XO4 ligand.

Example 4: Ex Vivo Staining of Mouse Brain Tissue

The ability of the Gd-containing Me-XO4-labeled liposomes of Example 2 to bind Aβ plaques was assessed by staining brain sections from APP/PSEN1 transgenic mouse line. The mice were engineered to progressively develop cortical and hippocampal plaques in an age-related manner similar to that observed in human AD pathology. Saggital sections (30 μm thick) from euthanized non-transgenic (control), 5, and 7 month old APP/PSEN1 mice were incubated in a 3 mM solution of the liposomes (concentration of Me-XO4 in the solution was 1 μM) for 2 h, at RT. This was followed by extensive washing with PBS to remove unbound liposomes. The stained tissues were mounted with VECTASHIELD® mounting media (Vector Laboratories, Inc., Burlingame, Calif.) to reduce background fluorescence and viewed under a confocal microscope.

Figure 3:
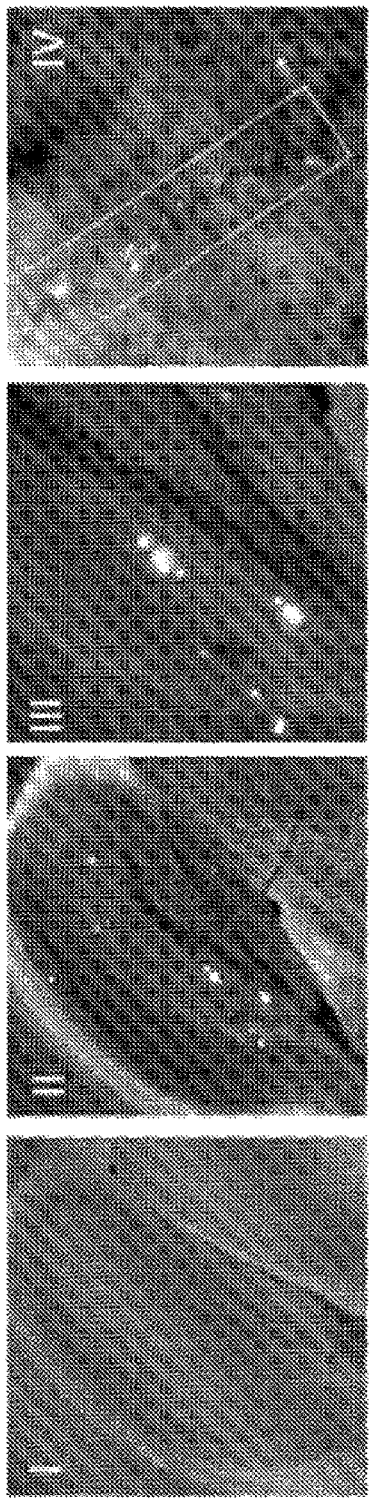
FIG. 3 illustrates example results of ex vivo staining of mouse brain tissue with Me-XO4-labeled liposomes.

As shown in FIG. 3, slides from the non-transgenic mice (panel I) showed no distinct fluorescent spots due to the absence of plaques. Distinct plaque deposits (panels II and III) as well as cerebral amyloid angiopathy (panel IV) were highlighted by the agent on brain sections from the 7 month old mice, but not the 5 months old mice. The same plaque deposition pattern was observed when similar sections were subjected to the same protocol with free methoxy-XO4 ligand.

Figure 4:
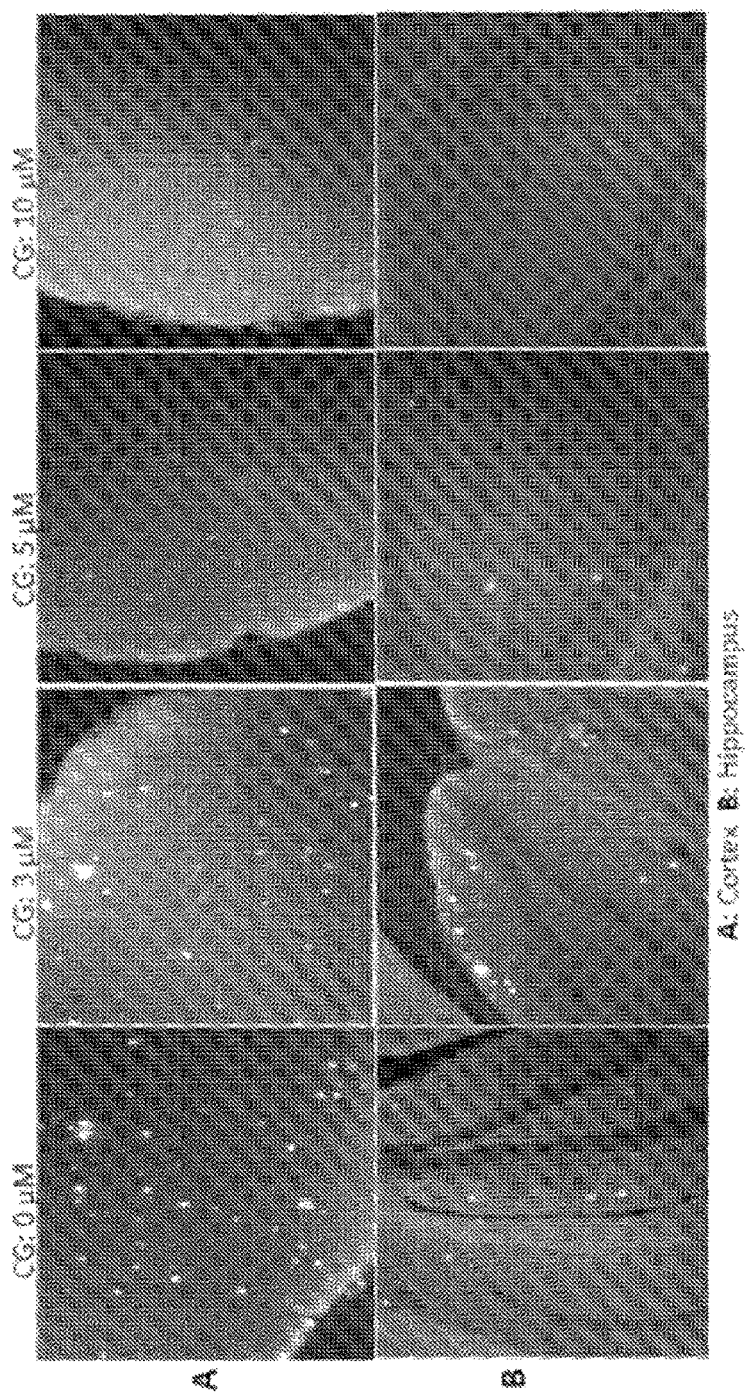
FIG. 4 illustrates example results of the competition between Me-XO4-labeled liposomes and CG for binding sites on Aβ plaque deposits on mouse brain tissue, ex vivo.

To further confirm the ability of the Gd-containing Me-XO4-labeled liposomes to selectively bind Aβ plaque deposits in brain tissue, the staining protocol was repeated with 1 μM Me-XO4 and increasing concentrations of CG. The results (FIG. 4) show a decrease in fluorescence intensity and the number of labeled plaques in both the cortex (A) and hippocampus (B), with increasing CG concentration.

Example 5: In Vivo Delivery of Gd-Containing Me-XO4-Labeled Liposomes to Cortical and Hippocampal Plaques in a 7 Month Old APP/PSEN1 Transgenic Mouse Line The Gd-containing Me-XO4-labeled liposomes were administered to 5 and 7 month old APP/PSEN1 mice by tail vain injection. 48 h following injection, the mice were euthanized and their brains sectioned for confocal light microscopic studies. Identical mice were injected with molecular/free methoxy-XO4 ligand to serve as a positive control, and with untargeted liposomes and saline as negative controls.

Figure 5:
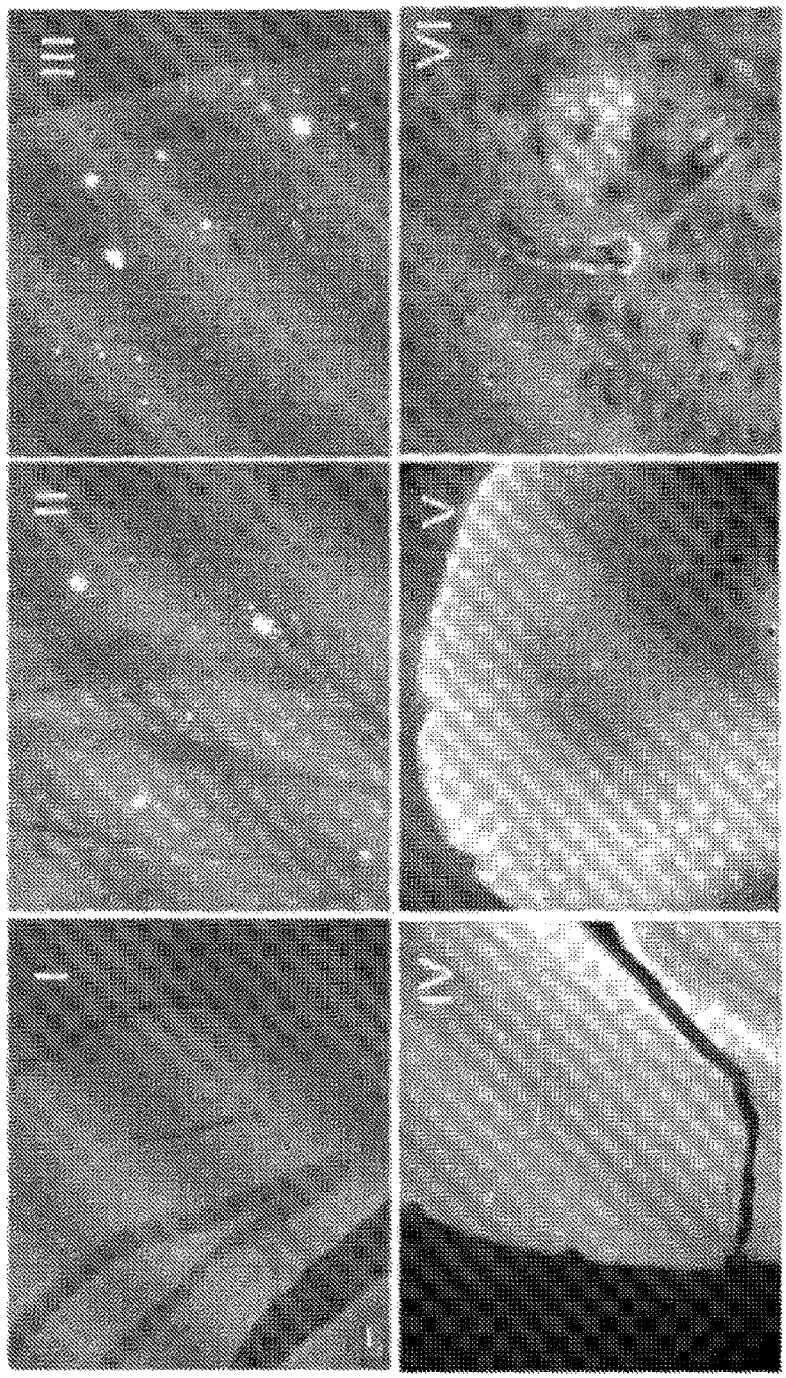
FIG. 5 illustrates example results of in vivo staining of mouse brain tissue with Me-XO4-labeled liposomes, and with free methoxy-XO4 ligand.

There was no noteworthy fluorescence (indicating the absence of plaques) when brain tissue sections from any of the 5 month old mice were imaged. Sections from the 7 month old mice (FIG. 5) injected with untargeted liposomes (panel I) and saline showed no fluorescence as well. Identical mice injected with free methoxy-XO4 ligand (panels II and III) revealed bright staining of both cortical and hippocampal plaques. Animals injected with Gd-containing Me-XO4 liposomes (panels IV, V, and VI) revealed similar plaque deposits and vascular pathology.

Figure 6:
FIG. 6 illustrates an optical reconstruction of example confocal microscope images from a sagittal section of a mouse brain injected with Me-XO4-labeled liposomes.

Optical reconstruction of images on a slide from one of the nanoparticle treated mice in this study (FIG. 6) show localization of fluorescence predominantly in the cortex (top-most four arrows, in section A) and hippocampus (bottom-most four arrows, in section B). The Gd-containing Me-XO4 liposomes penetrated the BBB barrier and pervasively migrated through the brain.

Example 6: Inflammatory Potential of Me-XO4

Inflammation around the amyloid deposit is considered to be a major risk factor for the progression of AD. Thus, it is highly desirable for imaging agents to present a low or reduced inflammation risk. Phospholipid-AL-PEG-ligand conjugates generally tend to be inflammatory in nature. Indeed, lipopolysaccharides ("LPS"), which are similar to phospholipid-AL-PEG-ligand conjugates in structure, are among the most inflammatory compositions known.

The inflammatory potential of Me-XO4 was compared to free (i.e., unconjugated) methoxy-XO4 ligand, LPS, and an untreated control ("UTC"). Translocation of NF-kb from cytosol to the nucleus is an early event in the inflammatory reaction. Upon receiving the inflammatory potential, NF-kb moves from the cytoplasm to the nucleus and induces gene transcription. Therefore translocation of NF-kB is a widely used marker for inflammation. In brief, the protocol is outlined below.

15,000 HeLa cells were plated in each of 96 well plates and allowed to stand overnight. The cells were treated with the different concentrations of the test compounds for 2 h in a 37° C. incubator. The positive controls were treated with 1 mg/mL LPS. At the end of the incubation period, the medium was aspirated and the cells were washed with PBS. The cells were treated with 4% paraformaldehyde (to fix the cells) for 10 min at RT. The cells were washed twice with ice cold PBS. The cells were incubated with 0.25% Triton-X-100 in PBS for 10 min at RT, and were again washed three times (5 min each wash) with PBS. The cells were incubated with 1% BSA in PBS-T (PBS with 0.1% Tween-20) for 45 min at RT. At the end of the incubation period, the cells were further incubated with primary antibody against NF-kBat 1:50 dilution in PBST for 1 h at RT. The cells were again washed with PBS three times (5 min each). The cells were incubated with the secondary antibody in PBST for 1 h at RT, and were again washed three times (5 min each) with PBS. 100 µl of DAPI (1 µg/mL) was placed in each well and kept at 4° C. until further analysis. The cells were scanned on a Cell Lab IC-100 image cytometer (Beckman-Coulter, Fullerton, Calif.). The data were further analyzed using CyteSeer software (Vala Sciences, San Diego, Calif.), and represented as Pearson's Correlation coefficient (PCC) of the protein intensity present over the nuclear mask.

Figure 7:
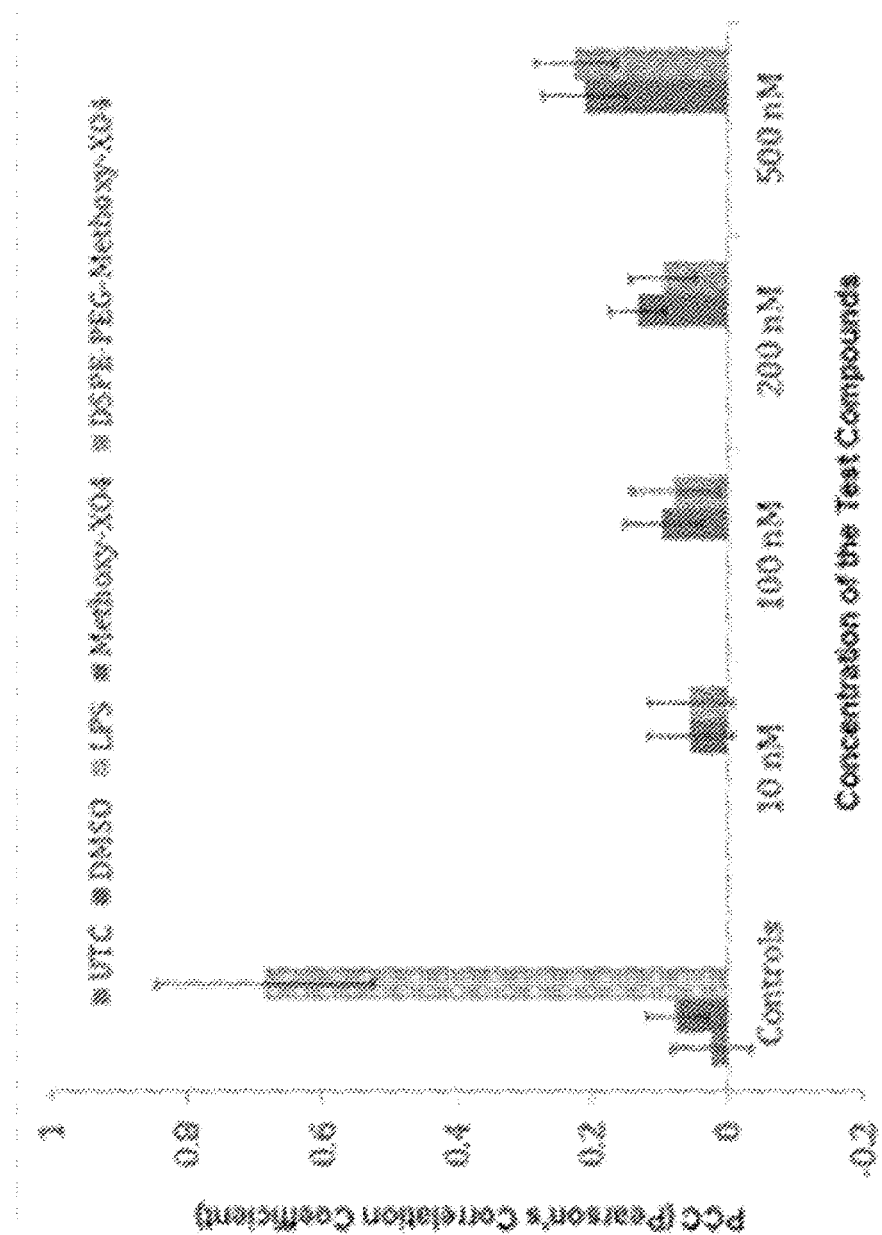
FIG. 7 illustrates an example comparison of inflammatory potential between free methoxy-XO4 ligand and the Me-XO4 conjugate.

Surprisingly, Me-XO4 was found to be less inflammatory than free methoxy-XO4 ligand at all but the highest concentrations (500 nM) tested. The results are depicted in FIG. 7. Thus, it is a particular teaching of at least one embodiment herein that the conjugated and/or liposomal amyloid binding ligand is less (or at least not more) inflammatory than the free ligand.

Example 7: Cytotoxicity of Me-XO4

The cytotoxicity of Me-XO4 was compared to free (i.e., not conjugated) methoxy-XO4 ligand and an untreated control. The toxicity of the test compounds was evaluated using standard MTT assays. 15,000 HeLa cells were plated in each of 96 well plates and allowed to stand overnight. The cells were treated with three different concentrations of the test compounds for 2 h in a 37° C. incubator. The positive controls were treated with 1 mg/mL LPS. At the end of the incubation period, a MTS cell toxicity assay kit (CELLTITER 96® AQueous Assay kit, Promega, Madison Wis.) was used according to the manufacturer's protocol. At the end of the incubation period, cells were treated with 15 µL MTS reagent/100 µL media for 3 h at 37° C. After 3 h of incubation, the absorbance was recorded at 490 nm using a plate reader.

Figure 8:
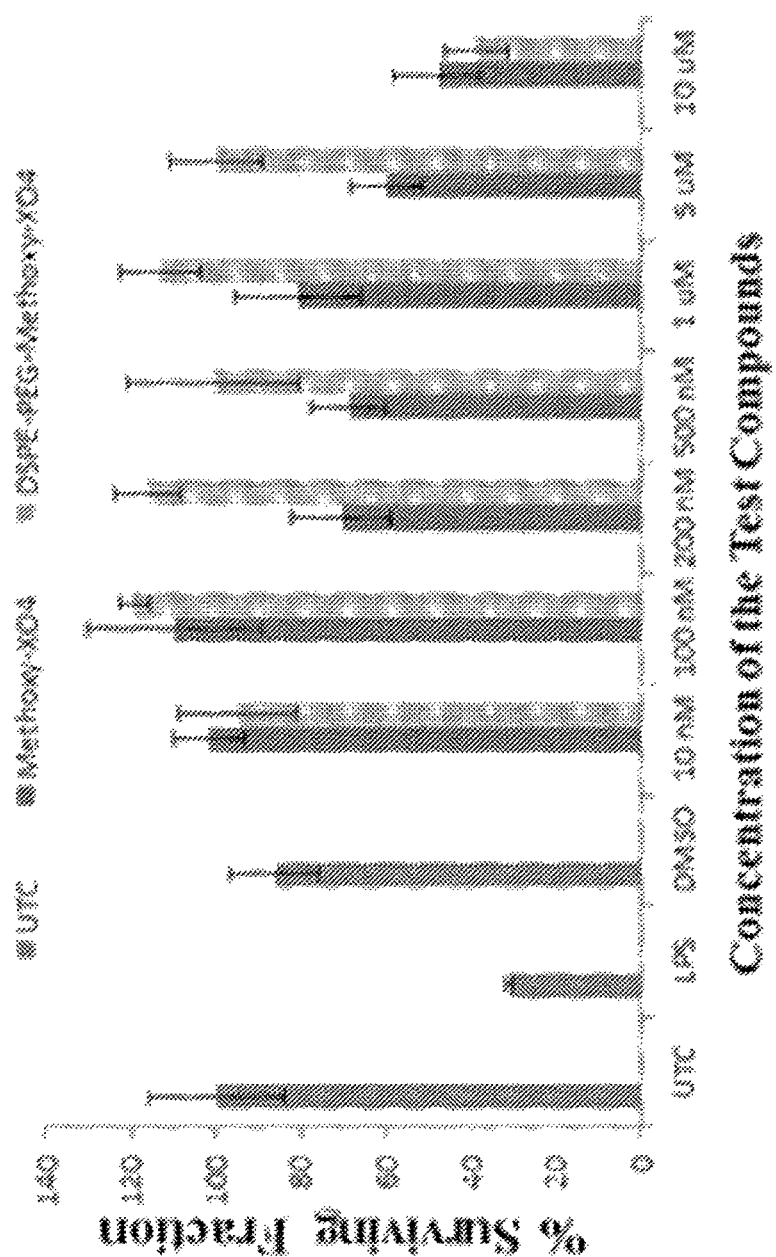
FIG. 8 illustrates an example comparison of cellular toxicity between free methoxy-XO4 ligand and the Me-XO4 conjugate.

Surprisingly, Me-XO4 was found to be less cytotoxic than free methoxy-XO4 ligand. The results are depicted in FIG. 8. Thus, it is a particular teaching of at least one embodiment herein that the conjugated and/or liposomal amyloid binding ligand is less (or at least not more) toxic than the free ligand.

Figure 9A:
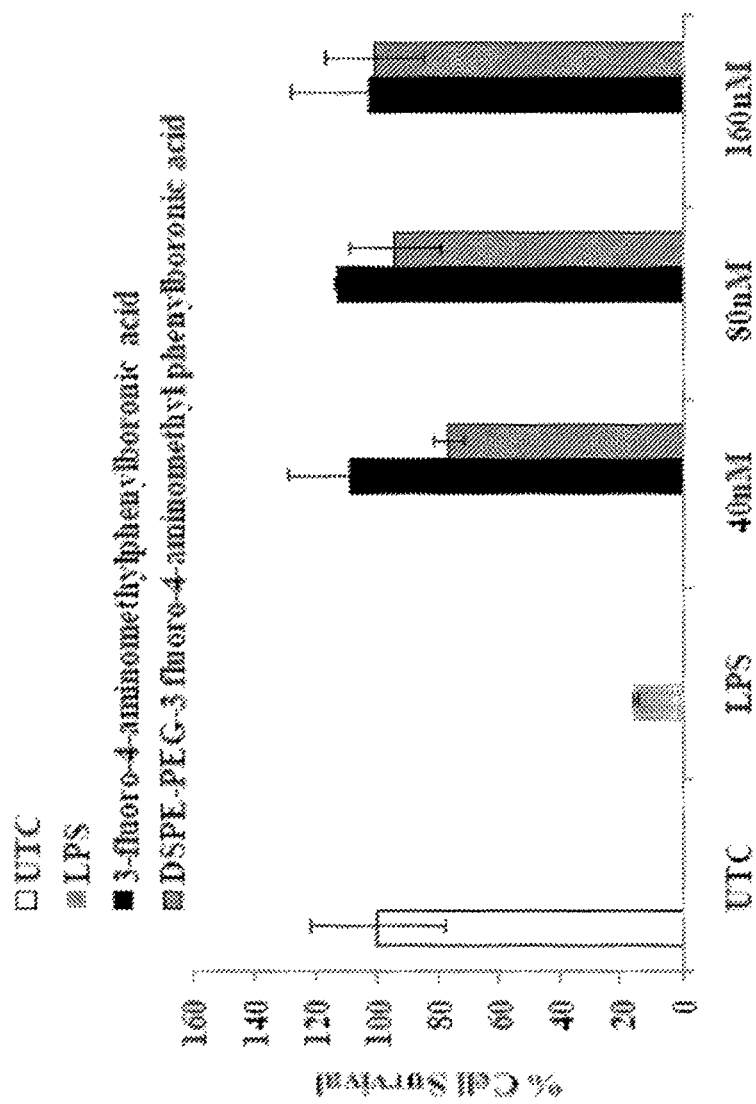
FIG. 9A illustrates a comparison of cellular toxicity between DSPE-AL-PEG-3-fluoro-4-aminomethylphenyl boronic acid conjugate and the free ligand, 3-fluoro-4-aminomethylphenyl boronic acid.

(Comparative) Example 8: Cytotoxicity and Inflammatory Potential of Boronic Acid Ligand Upon Conjugation to a Phospholipid-AL-PEG Anchor The cytotoxicity of 3-fluoro-4-aminomethylphenylboronic acid was compared to the conjugated ligand, namely DSPE-AL-PEG-3-fluoro-4-aminomethylphenylboronic acid, LPS, and an untreated control, according to the same protocols as described above in Example 7. FIG. 9A illustrates the surviving fraction of cells. As expected, the conjugated ligand is significantly more cytotoxic than the free ligand.

Figure 9B:
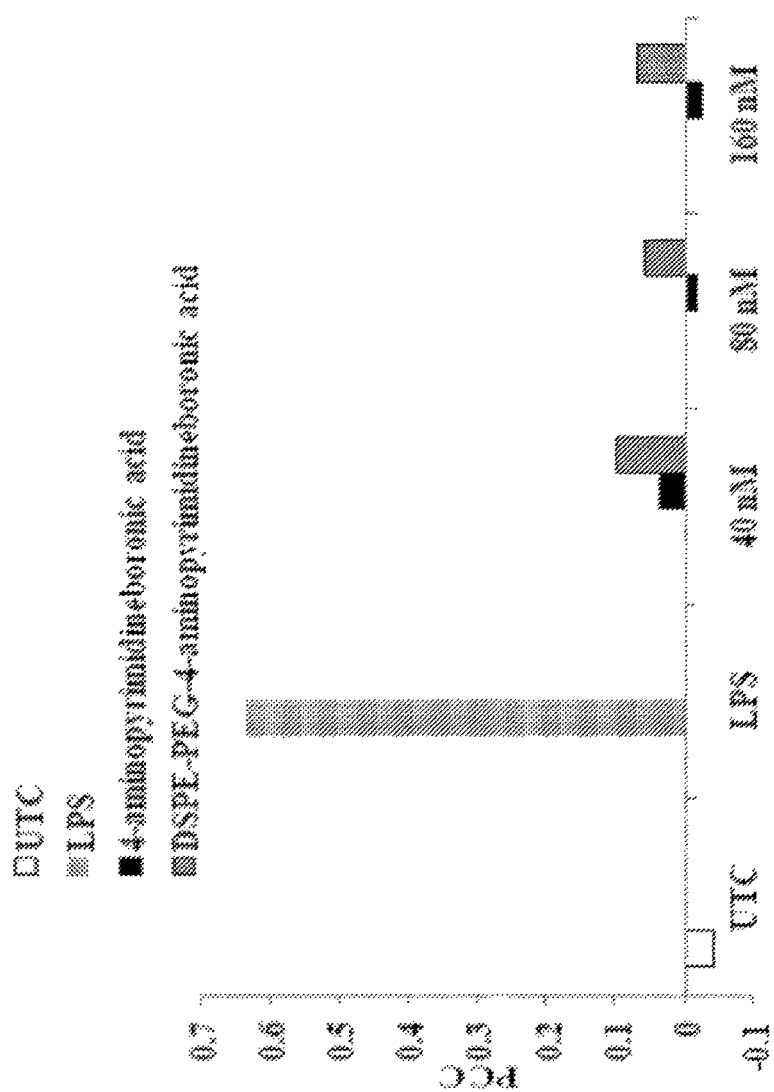
FIG. 9B illustrates a comparison of inflammatory potential between DSPE-AL-PEG-4-aminopyrimidine boronic acid conjugate and the free ligand, 4-aminopyrimidine boronic acid.

The inflammatory potential of 4-aminopyrimidine boronic acid was compared to the conjugated ligand, namely DSPE-AL-PEG-4-aminopyrimidine boronic acid, LSP, and an untreated control, according to the same protocols as described above in Example 6. FIG. 9B depicts the PCC between the nuclear and cytoplasmic fractions of $NF_KB$ molecule in HeLa cells. As expected, the conjugated ligand is significantly more inflammatory than the free ligand.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include ±10% of the number. For example, "about 10" may mean from 9 to 11.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:
1. A liposomal composition, comprising:
   a membrane, comprising:
      a first phospholipid;
      cholesterol;
      a second phospholipid, the second phospholipid being derivatized with a polymer;
      a third phospholipid, the third phospholipid being a phospholipid-polymer-aromatic compound conjugate, the phospholipid-polymer-aromatic compound conjugate being represented by:

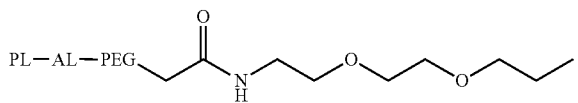

-continued

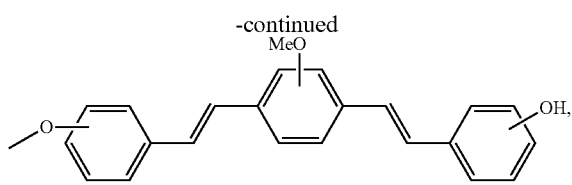

wherein: PL is a phospholipid; AL is an aliphatic linkage; and PEG is a polyethylene glycol polymer; and
a nonradioactive magnetic resonance imaging (MRI) contrast enhancing agent at least one of encapsulated by or bound to the membrane.

2. The liposomal composition of claim 1, wherein AL comprises one or more of: a carbamate linkage and an amide linkage.

3. The liposomal composition of claim 1, the phospholipid-polymer-aromatic compound conjugate comprising a compound represented by:

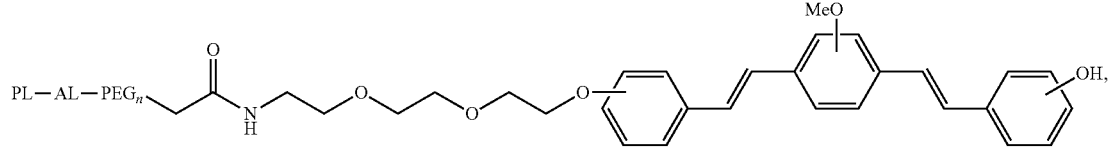

wherein n represents a degree of polymerization of the polyethylene glycol polymer between about 10 to about 100.

4. The liposomal composition of claim 3, wherein n is about 30 to about 80.

5. The liposomal composition of claim 1, the phospholipid-polymer-aromatic compound conjugate comprising a compound represented by:

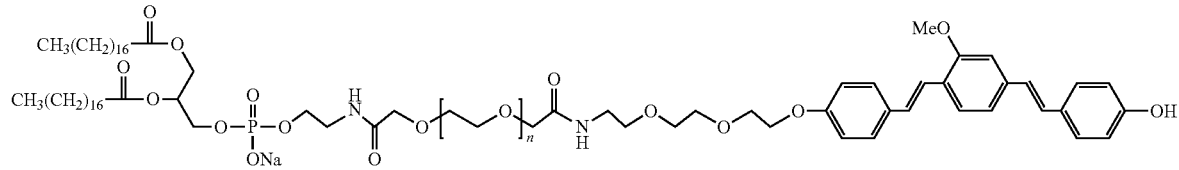

wherein n is about 10 to about 100.

6. The liposomal composition of claim 1, wherein the nonradioactive MRI contrast enhancing agent comprises gadolinium.

7. The liposomal composition of claim 1, comprising:
DPPC as the first phospholipid;
the cholesterol;
DSPE-AL-mPEG-2000 as the second phospholipid;
the third phospholipid, comprising a compound represented by:

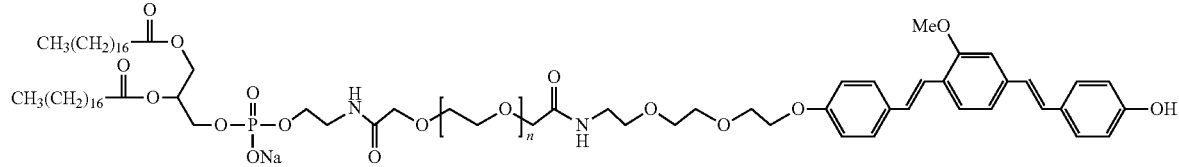

wherein n is about 10 to about 100; and
the nonradioactive magnetic resonance imaging (MRI) contrast enhancing agent comprising Gd-DTPA-BSA.

8. A method for imaging amyloid deposits in a patient, the method comprising:
introducing into the patient a detectable quantity of a liposomal composition comprising:
a membrane, comprising:
a first phospholipid;
cholesterol;
a second phospholipid, the second phospholipid derivatized with a polymer; and
a third phospholipid, the third phospholipid being a phospholipid-polymer-aromatic compound conjugate represented by:

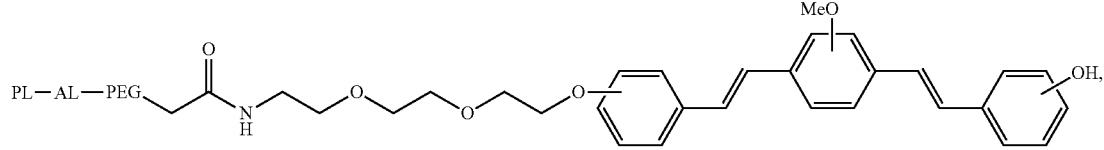

wherein: PL is a phospholipid; AL is an aliphatic linkage; and
PEG is a polyethylene glycol polymer; and
a nonradioactive magnetic resonance imaging (MRI) contrast enhancing agent at least one of encapsulated by or bound to the membrane;
allowing sufficient time for the liposomal composition to be associated with one or more amyloid deposits; and
detecting the liposomal composition associated with the one or more amyloid deposits.

9. The method of claim 8, wherein the nonradioactive MRI contrast enhancing agent comprises gadolinium.

10. The method of claim 8, wherein the detecting comprises detecting using magnetic resonance imaging.

11. The method of claim 8, wherein AL comprises one or more of: an amide linkage and a carbamate linkage.

12. The method of claim 8, the phospholipid-polymer-aromatic compound conjugate comprising a compound represented by:

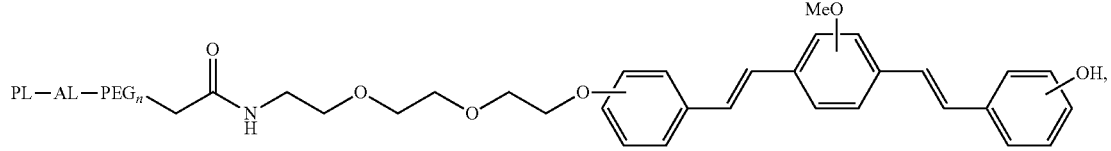

wherein n represents a degree of polymerization of the polyethylene glycol polymer of about 10 to about 100.

13. The method of claim 8, the phospholipid-polymer-aromatic compound conjugate comprising a compound represented by:

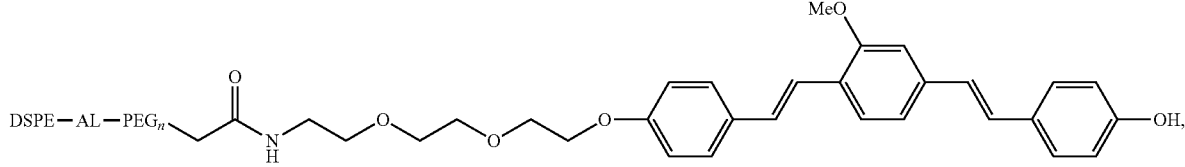

wherein n represents a degree of polymerization of the polyethylene glycol polymer of about 10 to about 100.

14. The method of claim 13, wherein n is about 30 to about 80.

15. The method of claim 8, the phospholipid-polymer-aromatic compound conjugate comprising a compound represented by:

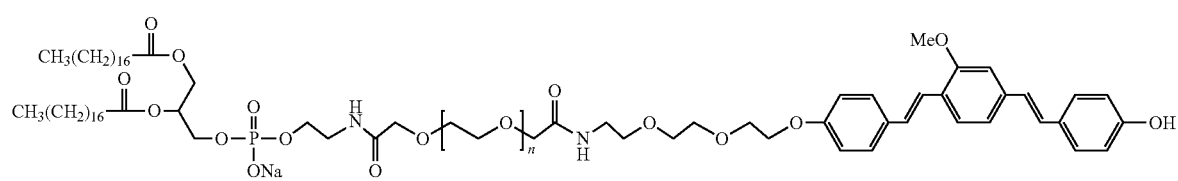

wherein n is about 10 to about 100.

16. A phospholipid-polymer-aromatic compound conjugate, represented by:

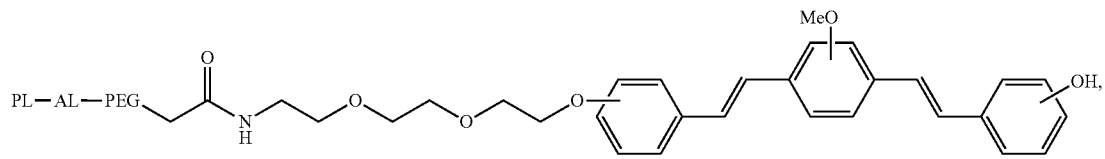

wherein:
  PL is a phospholipid;
  AL is an aliphatic linkage; and
  PEG is a polyethylene glycol polymer.

17. The phospholipid-polymer-aromatic compound conjugate of claim 16, wherein AL comprises one or more of: an amide linkage and a carbamate linkage.

18. The phospholipid-polymer-aromatic compound conjugate of claim 16, represented by:

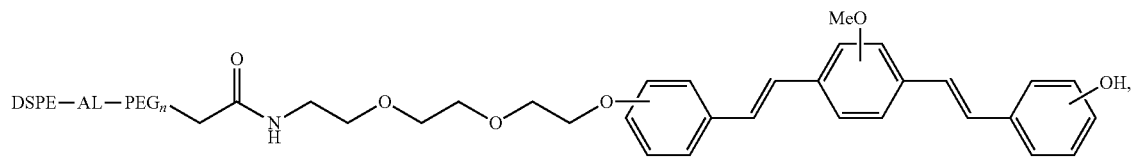

wherein n represents a degree of polymerization of the polyethylene glycol polymer of about 10 to about 100.

19. The phospholipid-polymer-aromatic compound conjugate of claim 16, comprising one of:

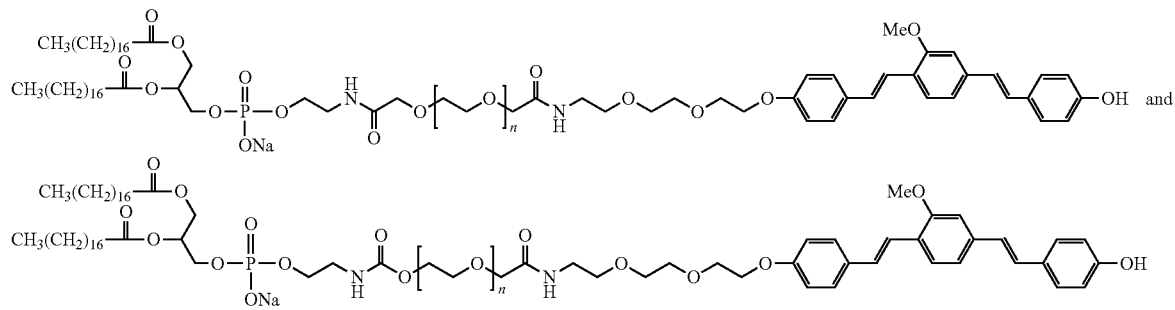

wherein each n is independently about 10 to about 100.

20. The phospholipid-polymer-aromatic compound conjugate of claim 19, wherein each n is independently about 30 to about 80.

* * * * *